United States Patent
Abrams et al.

(10) Patent No.: US 11,504,374 B2
(45) Date of Patent: *Nov. 22, 2022

(54) COMPOSITIONS AND METHODS FOR THE TREATMENT OF A BETA-CATENIN-ASSOCIATED DISEASE OR DISORDER

(71) Applicant: Dicerna Pharmaceuticals, Inc., Lexington, MA (US)

(72) Inventors: Marc Abrams, Natick, MA (US); Shanthi Ganesh, Shrewsbury, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 59 days.

This patent is subject to a terminal disclaimer.

(21) Appl. No.: 17/036,369

(22) Filed: Sep. 29, 2020

(65) Prior Publication Data

US 2021/0015820 A1 Jan. 21, 2021

Related U.S. Application Data

(62) Division of application No. 16/084,852, filed as application No. PCT/US2017/022510 on Mar. 15, 2017, now Pat. No. 10,821,112.

(60) Provisional application No. 62/365,164, filed on Jul. 21, 2016, provisional application No. 62/318,529, filed on Apr. 5, 2016, provisional application No. 62/309,449, filed on Mar. 16, 2016.

(51) Int. Cl.
| | |
|---|---|
| *C12N 15/113* | (2010.01) |
| *A61K 31/519* | (2006.01) |
| *A61K 31/7088* | (2006.01) |
| *A61K 9/00* | (2006.01) |
| *A61P 35/00* | (2006.01) |
| *A61K 9/51* | (2006.01) |

(52) U.S. Cl.
CPC .......... *A61K 31/519* (2013.01); *A61K 9/0019* (2013.01); *A61K 9/5123* (2013.01); *A61K 31/7088* (2013.01); *A61P 35/00* (2018.01); *C12N 15/113* (2013.01); *C12N 2310/14* (2013.01)

(58) Field of Classification Search
CPC ... A61K 2300/00; A61P 35/00; C12N 15/113; C12N 2310/14
See application file for complete search history.

(56) References Cited

U.S. PATENT DOCUMENTS

| 8,198,427 | B1 | 6/2012 | Khvorova et al. | |
| 10,821,112 | B2* | 11/2020 | Abrams | C12N 15/113 |
| 2003/0203865 | A1 | 10/2003 | Harvie et al. | |
| 2013/0109740 | A1 | 5/2013 | Brown et al. | |
| 2013/0137752 | A1 | 5/2013 | Brown et al. | |
| 2014/0343126 | A1 | 11/2014 | Brown et al. | |
| 2015/0071930 | A1 | 3/2015 | Lee et al. | |
| 2015/0073033 | A1 | 3/2015 | Lu et al. | |
| 2015/0240234 | A1 | 8/2015 | Brown et al. | |
| 2015/0291954 | A1 | 10/2015 | Bettencourt et al. | |
| 2015/0297626 | A1 | 10/2015 | van Haastert et al. | |
| 2016/0015688 | A1 | 1/2016 | Wang et al. | |

FOREIGN PATENT DOCUMENTS

| WO | 2012/018754 A1 | 2/2012 |
| WO | 2013/066944 A1 | 5/2013 |
| WO | 2013/105022 A1 | 7/2013 |
| WO | 2015/051252 A1 | 4/2015 |

OTHER PUBLICATIONS

International Search Report and Written Opinion dated Jun. 16, 2017 from International Application No. PCT/US2017/022510, 16 pages.

Juan et al., "Diminished WNT-β-catenin-c-MYC signaling is a barrier for malignant progression of BRAFV600E-induced lung tumors", Genes and Development, Jan. 20, 2014, vol. 28, pp. 561-575.

JU174101, Genbank Accession No. JU174101, TSA: Crotalus adamanteus Cadam Catenin-b1, mRNA sequence, Aug. 17, 2012, https://www.ncbi.nlm.nih.gov/nuccore/JU174101, 2 pages.

LC140988, Genbank Accession No. LC140988, Elaphe quadrivirgata CTNNB1 mRNA for catenin (cadherin-associated protein), mRNA sequence, Sep. 13, 2016, https://www.ncbi.nlm.nih.gov/nuccore/LC140988, 2 pages.

LK065491, Genbank Accession No. LK065491, Apteryx australis mantelli genome assembly AptMant0, scaffold354, Jun. 17, 2015, https://www.ncbi.nlm.nih.gov/nuccore/LK065491.1, 1 page.

Supplementary European Search Report dated Nov. 27, 2019 for European Application No. 17767430.6, 13 pages.

Jiang et al., "Inactivation of the Wnt/β-catenin signaling pathway underlies inhibitory role of microRNA-129-5p in epithelial-mesenchymal transition and angiogenesis of prostate cancer by targeting ZIC2", Cancer Cell International, 2019, vol. 19, No. 271, 15 pages.

* cited by examiner

*Primary Examiner* — J. E. Angell
(74) *Attorney, Agent, or Firm* — MH2 Technology Law Group, LLP

(57) ABSTRACT

Disclosed herein are methods for the treatment of cancer, comprising administering to a subject β-catenin nucleic acid inhibitor molecule and a therapeutically effective amount of an MEK inhibitor or a c-Myc nucleic acid inhibitor molecule. Also disclosed herein is a pharmaceutical composition comprising a therapeutically effective amount of β-catenin nucleic acid inhibitor molecule; a therapeutically effective amount of an MEK inhibitor or a c-Myc nucleic acid inhibitor molecule and at least one pharmaceutical carrier.

19 Claims, 20 Drawing Sheets

Specification includes a Sequence Listing.

BCAT1

Passenger strand (sense)

5' AGAAUACAAAUGAUGUAGAAACAGCC 3' (SEQ ID NO: 1)

3' CGUCUUAUGUUUACUACAUCUUUGUCGGTGCUAUCGAU 5' (SEQ ID NO: 2)

Guide strand (antisense)

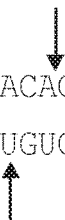 = cleavage points for Dicer protein

FIG. 7

MYC2

Passenger strand (sense)

5' AGCUUUUUUGCCCUGCGUGACCAGAC 3' (SEQ ID NO: 3)

3' CCUCGAAAAAACGGGACGCACUGGUCUGTGCUAUCGAU 5' (SEQ ID NO: 4)

Guide strand (antisense)

FIG. 8

MYC1

Passenger strand (sense)

5'-AGCUUUUUUGCCCUGCGUGACCAGA 3' (SEQ ID NO: 5)

3'-CCUCGAAAAAACGGGACGCACUGGUCU 5' (SEQ ID NO: 6)

Guide strand (antisense)

FIG. 9

COMPOSITIONS AND METHODS FOR THE TREATMENT OF A BETA-CATENIN-ASSOCIATED DISEASE OR DISORDER

CROSS-REFERENCE TO RELATED APPLICATIONS

This application is a divisional of U.S. patent application Ser. No. 16/084,852 (Allowed) filed 13 Sep. 2018, which is a U.S. National Stage application of PCT/US2017/022510 filed 15 Mar. 2017, which claims the benefit of, and relies on the filing date of, U.S. provisional patent application No. 62/309,449, filed 16 Mar. 2016; U.S. provisional patent application No. 62/318,529, filed 5 Apr. 2016; and U.S. provisional patent application No. 62/365,164, filed 21 Jul. 2016, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Mar. 10, 2017, is named 0243_0005-PCT_SL.txt and is 1,979 kilobytes in size.

FIELD

The present disclosure relates generally to combination therapy using a nucleic acid inhibitor molecule that reduces expression of the β-catenin gene and an inhibitor of a downstream β-catenin effector, such as c-Myc, or at least one inhibitor of the RAS/RAF/MEK/ERK signaling cascade, such as an MEK inhibitor.

BACKGROUND

β-catenin, an oncogene, is a key mediator of Wnt signaling in cells. β-catenin serves several cellular functions at multiple cellular locations, including the plasma membrane, where β-catenin contributes to the stabilization of intercellular adhesive complexes, the cytoplasm where β-catenin levels are regulated, and the nucleus where β-catenin is involved in transcriptional regulation and chromatin interactions.

Mutations in β-catenin (encoded by the CTNNB1 gene in humans) have been specifically associated with colorectal, desmoid, endometrial, gastric, hepatocellular, hepatoblastoma, kidney (Wilms' tumor), medulloblastoma, melanoma, ovarian (endometrioid), pancreatic, pilomatricoma, prostate, thyroid (anaplastic) and uterine (endometrium) cancers (Polakis P. Genes Dev. 14: 1837-51; Samowitz et al. Cancer Res. 59: 1442-4; Iwao et al. Cancer Res. 58: 1021-6; Mirabelli-Primdahl et al. Cancer Res. 59: 3346-51; Shitoh et al. J Clin Path. 52: 695-6; Tejpar et al. Oncogene 18: 6615-20; Kitaeva et al. Cancer Res. 57: 4478-81; Sparks et al. Cancer Res. 58: 1130-4; Miyaki et al. Cancer Res. 59: 4506-9; Park et al. Cancer Res. 59: 4257-60; Huang et al. Am J Pathol. 155: 1795-801; Nhieu et al. Am J Pathol. 155: 703-10; Legoix et al. Oncogene 18: 4044-6; Jeng et al. Cancer Lett. 152: 45-51; Koch et al. Cancer Res. 59: 269-73; Wei et al. Oncogene 19: 498-504; Koesters et al. Cancer Res. 59: 3880-2; Maiti et al. Cancer Res. 60: 6288-92; Zurawel et al. Cancer Res. 58: 896-9; Gamallo et al. Am J Pathol. 155: 527-36; Palacios and Gamallo Cancer Res. 58: 1344-7; Wright et al. Int J Cancer 82: 625-9; Gerdes et al. Digestion 60: 544-8; Chan et al. Nat Genet. 21: 410-3; Voeller et al. Cancer Res. 58: 2520-3; Garcia-Rostan et al. Cancer Res. 59: 1811-5; Fukuchi et al. Cancer Res. 58: 3526-8).

The β-catenin/Wnt pathway (see, e.g., FIG. 1) is consistently activated in over 80% of colorectal cancers. The role of β-catenin in the development of colorectal cancer has been shown to be regulated by the expression product of the APC (adenomatous polyposis of the colon) gene, a tumor suppressor. (Korinek et al., Science, 1997, 275:1784-1787; Morin et al., Science, 1997, 275:1787-1790). The APC protein normally binds β-catenin in conjunction with TCF/LEF forming a transcription factor complex. Morin et al. (Morin et al., Science, 1997, 275:1787-1790) report that APC protein down-regulates the transcriptional activation mediated by β-catenin and Tcf-4 in colon cancer. Their results indicated that the regulation of β-catenin is associated with APC's tumor suppressive effect and that this regulation can be circumvented by mutations in either APC or β-catenin.

Mutations in the β-catenin gene can be either truncations that lead to deletion of part of the N-terminus of β-catenin or point mutations that affect the serine and threonine residues that are targeted by components of the cytoplasmic destruction complex, such as GSK3α/β or CKIα, that mediate the phosphorylation of β-catenin and target its degradation by the proteosome. These mutant β-catenin proteins are refractory to phosphorylation and thus escape proteasomal degradations. Consequently, β-catenin accumulates within affected cells. Stabilized and nuclear-localized β-catenin is a hallmark of nearly all cases of colon cancer. (Clevers, H., 2006, Cell 127:469-480). Morin et al. demonstrated that mutations of β-catenin that altered phosphorylation sites rendered the cells insensitive to APC-mediated down-regulation of β-catenin and that this disrupted mechanism was important to colorectal tumorigenesis. (Morin et al., 1997, Science 275:1787-1790).

The KRAS gene is also commonly mutated in colorectal cancers (about 30-40%). KRAS is a member of the Ras family of oncogenes. It encodes a GTPase involved in intracellular signal transduction pathways. When activated, it recruits other signaling molecules, like c-Raf and PI 3-kinase. Mutations of KRAS also occur in over 90% of pancreatic cancers.

The β-catenin/Wnt pathway is consistently activated in over 50% of hepatocellular carcinoma (HCC) patients. Activated Wnt signaling and nuclear β-catenin correlate with recurrence of disease and poor prognosis (Takigawa et al. 2008, Curr Drug Targets November; 9 (11):1013-24). Elevated nuclear β-catenin staining has been documented in 17-66% of HCC patients (Zulehner et al. 2010, Am J Pathol. January; 176 (1):472-81; Yu et al. 2009, J Hepatol. May; 50 (50):948-57).

Despite advances in understanding how β-catenin functions as a key mediator of Wnt signaling in cells and how mutations and/or altered expression of β-catenin can play a role in tumorigenesis, there remains a need for compositions that can treat disease associated with CTNNB1 expression, such as cancer.

SUMMARY

The inventors herein have discovered that combining certain therapeutic approaches with nucleic acid inhibition of β-catenin can result in synergistic inhibition of tumor growth. In particular, combining β-catenin inhibition with MEK inhibition or combining β-catenin inhibition with c-Myc inhibition yields effective tumor inhibition (see, e.g., Examples 4-5 and FIGS. 4-6).

Disclosed herein are methods of treating a β-catenin-associated disease or disorder, comprising administering to a subject a therapeutically effective amount of a β-catenin nucleic acid inhibitor molecule and a therapeutically effective amount of an MEK inhibitor (such as trametinib) or a c-Myc nucleic acid inhibitor molecule. Administration of a β-catenin nucleic acid inhibitor molecule and a MEK inhibitor or a c-Myc nucleic acid inhibitor molecule can produce synergetic effects as compared to the administration of each agent individually.

In certain embodiments, the subject is a human.

Also provided is a pharmaceutical composition comprising a β-catenin nucleic acid inhibitor molecule for use in treating a β-catenin-associated disease or disorder, wherein the composition is administered in combination with a MEK inhibitor (such as trametinib) or a c-Myc nucleic acid inhibitor molecule. In certain embodiments, the β-catenin-associated disease or disorder is cancer, such as colorectal cancer, hepatocellular carcinoma, or melanoma.

In certain embodiments of these methods and compositions for use in treating β-catenin-associated disease or disorder, the β-catenin-associated disease or disorder is a β-catenin-associated cancer, such as colorectal cancer, hepatocellular carcinoma, or melanoma. In certain embodiments, the β-catenin-associated cancer has metastasized. In certain embodiments, the β-catenin-associated cancer is colorectal cancer that has metastasized. In certain embodiments, the colorectal cancer has metastasized to the liver. In certain embodiments of these methods and compositions for use in treating a β-catenin-associated disease or disorder, the MEK inhibitor is trametinib (GSK1120212), selumetinib, binimetinib (MEK162), cobimetinib (XL518), refametinib (BAY 86-9766), pimasertib, PD-325901, RO5068760, CI-1040 (PD035901), AZD8330 (ARRY-424704), RO4987655 (CH4987655), RO5126766, WX-554, E6201, and TAK-733. In one embodiment, the MEK inhibitor is trametinib.

In certain embodiments of these methods and compositions for use in treating a β-catenin-associated disease or disorder, the β-catenin nucleic acid inhibitor molecule or the c-Myc nucleic acid inhibitor molecule is formulated with a lipid nanoparticle.

Further disclosed herein are pharmaceutical compositions comprising a therapeutically effective amount of a β-catenin nucleic acid inhibitor molecule; a therapeutically effective amount of an MEK inhibitor or a c-Myc nucleic acid inhibitor molecule; and at least one pharmaceutical excipient.

Certain embodiments of the invention provide methods of treating a β-catenin-associated cancer in a subject, comprising administering to the subject: a therapeutically effective amount of a β-catenin nucleic acid inhibitor molecule; and a therapeutically effective amount of a MEK inhibitor, wherein prior to administering the β-catenin nucleic acid inhibitor molecule, the subject has undergone prior treatment for the β-catenin-associated cancer and developed resistance to that prior treatment. In certain of those embodiments, the prior treatment is administration of a MEK inhibitor. In certain embodiments, the MEK inhibitor of the prior treatment is trametinib. In certain embodiments, the MEK inhibitor administered to the subject is trametinib.

Certain embodiments of the invention provide methods of treating a β-catenin-associated cancer in a subject, comprising administering to the subjects a therapeutically effective amount of a β-catenin nucleic acid inhibitor molecule; and a therapeutically effective amount of a MEK inhibitor, wherein prior to administering the β-catenin nucleic acid inhibitor molecule, the subject has undergone at least two administrations of a prior treatment for the β-catenin-associated cancer. In certain of those embodiments, the subject has undergone at least three, four, five, six, or seven administrations of the prior treatment. In certain embodiments, the prior treatment is administration of a MEK inhibitor. In certain embodiments, the MEK inhibitor of the prior treatment is trametinib. In certain embodiments, the MEK inhibitor administered to the subject is trametinib.

Certain embodiments of the invention provide methods of treating a β-catenin-associated cancer in a subject, comprising administering to the subject: a therapeutically effective amount of a β-catenin nucleic acid inhibitor molecule; and a therapeutically effective amount of a MEK inhibitor, wherein the β-catenin associated cancer (e.g., colorectal cancer) has metastasized, for example, to the liver. In certain embodiments, the MEK inhibitor administered to the subject is trametinib.

Both the foregoing general summary and the following detailed description are exemplary only and are not restrictive of the disclosure.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

FIG. 3A) and LS174t (CTNNB1 and KRAS mutations; FIG. 3B) but not in the RKO colorectal tumor (FIG. 3C) having wild type APC and β-catenin genes.

FIG. 7 shows one non-limiting embodiment of a double-stranded β-catenin nucleic acid inhibitor molecule, having of a sense (or passenger) strand (SEQ ID NO: 1) and an antisense (guide) strand (SEQ ID NO: 2). This β-catenin nucleic acid inhibitor molecule is referred to herein as BCAT1.

FIG. 8 shows one non-limiting embodiment of a double-stranded c-Myc nucleic acid inhibitor molecule, having of a sense (or passenger) strand (SEQ ID NO: 3) and an antisense (guide) strand (SEQ ID NO: 4). This c-Myc nucleic acid inhibitor molecule is referred to herein as MYC2.

FIG. 9 shows one non-limiting embodiment of a double-stranded c-Myc nucleic acid inhibitor molecule, having of a sense (or passenger) strand (SEQ ID NO: 5) and an antisense (guide) strand (SEQ ID NO: 6). This c-Myc nucleic acid inhibitor molecule is referred to herein as MYC1.

DETAILED DESCRIPTION

Definitions

Figure 1:
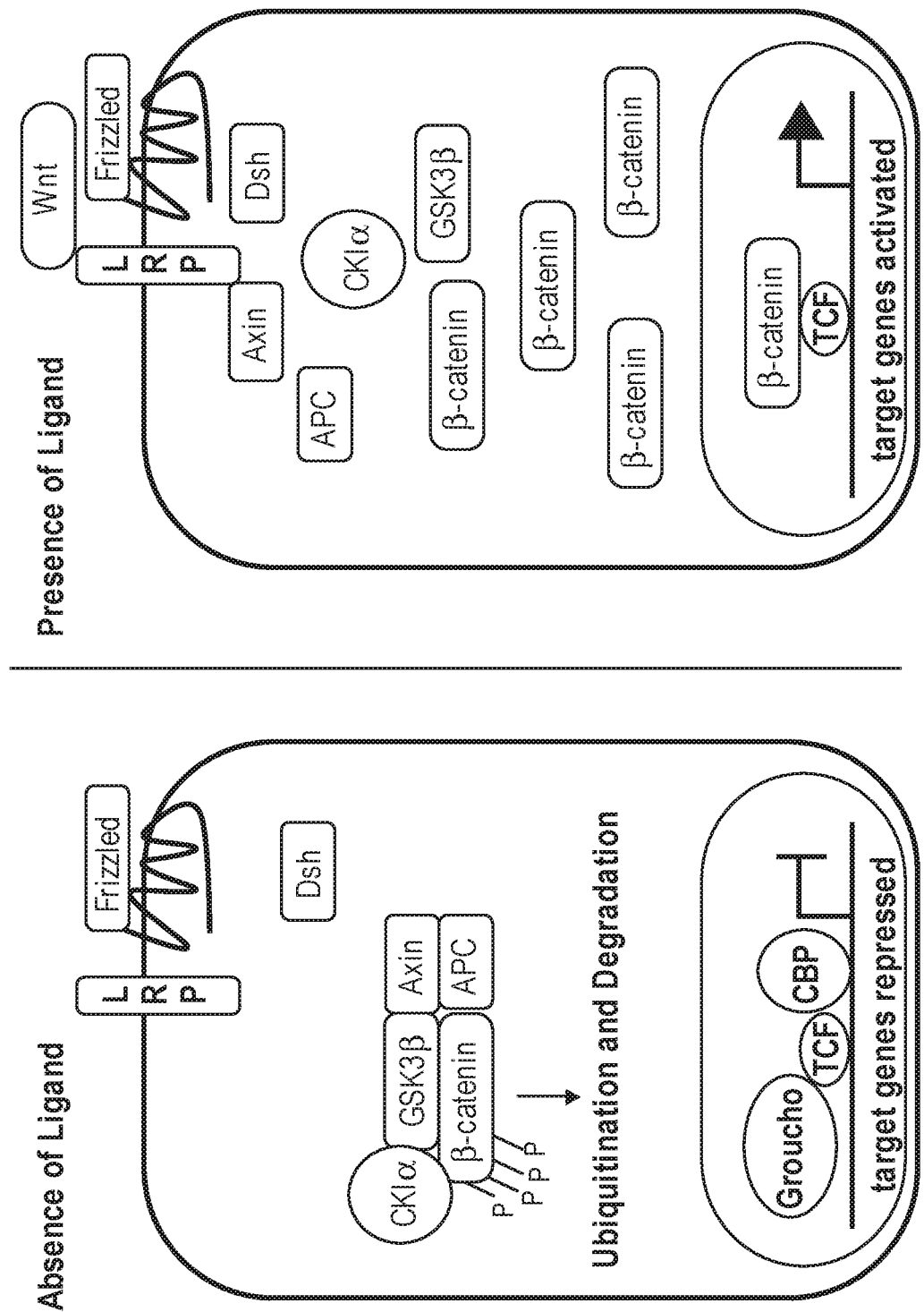
FIG. 1 shows a simplified diagram of the Wnt signaling pathway. The left side depicts a cell where the Wnt ligand is not bound to its surface receptor, β-catenin is sequestered in a destruction complex and targeted for degradation, and target genes are repressed. The right side depicts a cell after the Wnt ligand has bound its surface receptor, where the destruction complex disassembles, stabilized β-catenin is released and travels to the nucleus, and target genes are activated.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Administer: As used herein, "administering" a composition to a subject means to give, apply or bring the composition into contact with the subject. Administration can be accomplished by any of a number of routes, including, for example, topical, oral, subcutaneous, intramuscular, intraperitoneal, intravenous, intrathecal and intradermal.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

β-catenin: As used herein, "β-catenin" refers either to a polypeptide or a nucleic acid sequence encoding such a β-catenin protein. When referring to a polypeptide, "β-catenin" refers to the polypeptide gene product of a β-catenin gene/transcript (CTNNB1) (Genbank Accession Nos. NM_001904.3 (human β-catenin transcript variant 1), NM_001098209.1 (human β-catenin transcript variant 2), NM_001098210.1 (human β-catenin transcript variant 3), and NM_007614.2 & NM_007614.3 (mouse β-catenin).

β-catenin-associated: As used herein, a "β-catenin-associated" disease or disorder refers to a disease or disorder that is associated with altered β-catenin expression, level and/or activity. A "β-catenin-associated" disease or disorder includes cancer and/or proliferative diseases, conditions, or disorders, including colorectal, desmoid, endometrial, gastric, hepatocellular, hepatoblastoma, kidney (Wilms' tumor), medulloblastoma, melanoma, ovarian (endometrioid), pancreatic, pilomatricoma, prostate, thyroid (anaplastic) and uterine (endometrium) cancers. In one embodiment, the β-catenin-associated disease or disorder is colorectal cancer, hepatocellular carcinoma, or melanoma.

BCAT1: As used herein "BCAT1" refers to a nucleic acid inhibitor molecule that targets the β-catenin gene and has a sense strand with a nucleic acid sequence consisting of SEQ ID NO:1 and an antisense strand with a nucleic acid sequence consisting of SEQ ID NO:2.

C-Myc: As used herein, "c-Myc" refers to either to a polypeptide or a nucleic acid sequence encoding such a c-Myc protein (such as Genbank Accession Nos. NP_002458.2 and NP_034979.3). c-Myc transcripts include the sequences of Genbank Accession Nos. NM_002467.4 and NM_010849.4.

MYC1: As used herein "MYC1" refers to a nucleic acid inhibitor molecule that targets the c-Myc gene and has a sense strand with a nucleic acid sequence consisting of SEQ ID NO:5 and an antisense strand with a nucleic acid sequence consisting of SEQ ID NO:6.

MYC2: As used herein "MYC2" refers to a nucleic acid inhibitor molecule that targets the c-Myc gene and has a sense strand with a nucleic acid sequence consisting of SEQ ID NO: 3 and an antisense strand with a nucleic acid sequence consisting of SEQ ID NO: 4.

MEK Inhibitor As used herein, the term "MEK inhibitor" refers to a compound or agent that reduces an activity of the mitogen-activated protein kinase kinase enzyme MEK1 and/or MEK2.

Excipient: As used herein, the term "excipient" refers to a non-therapeutic agent that may be included in a composition, for example to provide or contribute to a desired consistency or stabilizing effect.

Nucleic acid inhibitor molecule: As used herein, the term "nucleic acid inhibitor molecule" refers to an oligonucleotide molecule that reduces or eliminates the expression of a target gene wherein the oligonucleotide molecule contains a region that specifically targets a sequence in the target gene mRNA. Typically, the targeting region of the nucleic acid inhibitor molecule comprises a sequence that is sufficiently complementary to a sequence on the target gene mRNA to direct the effect of the nucleic acid inhibitor molecule to the specified target gene. For example, a "β-catenin nucleic acid inhibitor molecule" reduces or eliminates the expression of a CTNNB1 gene, and a "c-Myc nucleic acid inhibitor molecule" reduces or eliminates the expression of a c-Myc gene. The nucleic acid inhibitor molecule may include natural ribonucleotides, natural deoxyribonucleotides, and/or modified nucleotides. The modified nucleotides include modifications such as substitution on positions on the sugar ring, modifications of the phosphoester linkages between nucleotides, non-natural bases, and non-natural alternative carbon structures such as locked nucleic acids ("LNA") (see below) and unlocked nucleic acids ("UNA") (see below).

Reduce(s): The term "reduce" or "reduces" as used herein refers to its meaning as is generally accepted in the art. With reference to exemplary nucleic acid inhibitor molecules (e.g., β-catenin and c-Myc siNA molecules) or exemplary inhibitors (e.g., MEK inhibitor), the term generally refers to the reduction in the expression of a gene, or level of RNA molecules or equivalent RNA molecules encoding one or more proteins or protein subunits, or activity of one or more proteins or protein subunits, below that observed in the absence of the nucleic acid inhibitor molecules or inhibitor.

Resistance: The term "resistance" as used herein refers to the condition that occurs when a treatment that previously reduced or inhibited tumor growth in a subject no longer reduces or inhibits tumor growth in that subject.

RNAi inhibitor molecule: The term "RNAi inhibitor molecule" as used herein refers to either (a) a double stranded nucleic acid inhibitor molecule ("dsRNAi inhibitor molecule") having a sense strand (passenger) and antisense strand (guide), where the antisense strand is used by the Argonaute 2 (Ago 2) endonuclease in the cleavage of the target mRNA or (b) a single stranded nucleic acid inhibitor molecule ("ssRNAi inhibitor molecule") having a single antisense strand that is used by Ago2; where the RNAi inhibitor molecule makes use of at least part of the cell's RNA interference ("RNAi") machinery to reduce or eliminate expression of the target gene.

Subject: As used herein, the term "subject" means any mammal, including mice, rabbits, and humans. In one embodiment, the subject is a human. The terms "individual" or "patient" are intended to be interchangeable with "subject."

Nucleic Acid Inhibitor Molecules

Various structures have been used for nucleic acid inhibitor molecules. For example, early work focused on double-stranded nucleic acid molecules with each strand having sizes of 19-25 nucleotides with at least one 3' overhang of 1 to 5 nucleotides (see, e.g., U.S. Pat. No. 8,372,968). Subsequently, longer double-stranded RNA molecules that get processed in vivo by the Dicer enzyme to active siRNA molecules were developed (see, e.g., U.S. Pat. No. 8,883,996). Later work developed extended double-stranded nucleic acid inhibitor molecules where at least one end of at least one strand is extended beyond the double-stranded targeting region of the molecule, including structures where one of the strands includes a thermodynamically-stabilizing tetraloop structure (see, e.g., U.S. Pat. Nos. 8,513,207, 8,927,705, and WO 2010/033225, which are incorporated by reference for their disclosure of these double-stranded nucleic acid inhibitor molecules). Those structures include single-stranded extensions (on one or both sides of the molecule) and double-stranded extensions. Furthermore, recent efforts have demonstrated activity of single-stranded RNAi molecules (see, e.g., Matsui et al. (2016), Molecular Therapy, accepted article preview online Feb. 23, 2016; doi: 10.1038/mt.2016.39). And, antisense molecules have been used for decades to reduce expression of specific target genes. A number of variations on the common themes of these structures have been developed for a range of targets. The β-catenin and c-Myc nucleic acid inhibitor molecules of the present invention can be based on any of the above structures and their variations described in the literature. β-catenin and c-Myc nucleic acid inhibitor molecules also include micro-RNA (miRNA) and short hairpin RNA (shRNA) molecules, such as those described in U.S. Published Application No. 2009/0099115.

Typically, many of the nucleotide subunits of the nucleic acid inhibitor molecules are modified to improve various characteristics of the molecule such as resistance to nucleases or lowered immunogenicity, (see, e.g., Bramsen et al. (2009), Nucleic Acids Res., 37, 2867-2881). In certain embodiments, every nucleotide of a nucleic acid inhibitor molecule is modified. In certain embodiments, substantially all of the nucleotides of a nucleic acid inhibitor molecule are modified. In certain embodiments, more than half of the nucleotides of a nucleic acid inhibitor molecule are modified. In certain embodiments, less than half of the nucleotides of a nucleic acid inhibitor molecule are modified. In certain embodiments, none of the nucleotides of a nucleic acid inhibitor molecule are modified. Modifications can occur in groups on the oligonucleotide chain or different modified nucleotides can be interspersed.

Many nucleotide modifications have been used in the oligonucleotide field. Modifications can be made on any part of the nucleotide, including the sugar moiety, the phosphoester linkage, and the nucleobase. Typical examples of nucleotide modification include, but are not limited to, 2'-fluoro-, 2'-OMethyl-, and 5-methylcytosine. In certain embodiments, the nucleic acid inhibitor molecules of the invention include one or more deoxyribonucleotides. Typically, the nucleic acid inhibitor molecules contain fewer than 5 deoxyribonucleotides. In certain embodiments, the nucleic acid inhibitor molecules of the invention include one or more ribonucleotides.

In certain embodiments, the ring structure of the sugar moiety is modified, including, but not limited to, Locked Nucleic Acids ("LNA") (see, e.g., Koshkin et al. (1998), Tetrahedron 54, 3607-3630) and Unlocked Nucleic Acids ("UNA") (see, e.g., Snead et al. (2013), Molecular Therapy-Nucleic Acids, 2, e103 (doi: 10.1038/mtna.2013.36)).

The 5' end of the oligonucleotide is an oft modified position. In certain embodiments, a hydroxyl group is attached to the 5' end of the oligonucleotide of a nucleic acid inhibitor molecule of the invention. In certain embodiments, a phosphate group is attached to the 5' end of the oligonucleotide of a nucleic acid inhibitor molecule of the invention. In certain embodiments, the 5' end is attached to chemical moiety that mimics the electrostatic and steric properties of a phosphate group ("phosphate mimic") (see, e.g., Prakash et al. (2015), Nucleic Acids Res., advance access published Mar. 9, 2015 (doi: 10.1093/narlgkvl62). Many phosphate mimics have been developed that can be attached to the 5' end (see, e.g., U.S. Pat. No. 8,927,513). Other modifications have been developed for the 5' end of oligonucleotides (see, e.g., WO 2011/133871).

β-Catenin Nucleic Acid Inhibitor Molecules

As disclosed herein, a β-catenin nucleic acid inhibitor molecule can be combined with an MEK inhibitor or a c-Myc nucleic acid inhibitor molecule for treating β-catenin-associated disease or disorders, such as cancer. We have shown that these combinations can produce synergetic effects as compared to the administration of each agent individually.

β-catenin nucleic acid inhibitor molecules are known, as disclosed, for example, in U.S. Published Application Nos. 2015/0291954 and 2015/0291956 and U.S. Pat. Nos. 6,066,500; 8,198,427; 8,835,623; or 9,243,244, which are incorporated by reference for their disclosure of these β-catenin nucleic acid inhibitor molecules. In certain embodiments, the β-catenin nucleic acid inhibitor molecule is a molecule disclosed in U.S. Pat. No. 9,243,244.

In certain embodiments, the β-catenin nucleic acid inhibitor molecules of the invention are dsRNAi inhibitor molecules where the double-stranded region of the molecule is between 15 and 40 nucleotides in length. In certain of those embodiments, the double-stranded region is between 20 and 30 nucleotides in length. In certain of those embodiments, the double-stranded region is 21, 22, 23, 24, 25, or 26 nucleotides in length.

In certain embodiments, the β-catenin nucleic acid inhibitor molecules of the invention are dsRNAi inhibitor molecules where the sense strand is between 18 and 66 nucleotides in length. In certain of those embodiments, the sense strand is between 25 and 45 nucleotides in length. In certain embodiments, the sense strand is between 30 and 40 nucleotides in length. In certain embodiments, the sense strand is 36, 37, 38, 39, or 40 nucleotides in length. In certain embodiments, the sense strand is between 25 and 30 nucleotides in length. In certain of those embodiments, the sense strand is 25, 26, or 27 nucleotides in length.

In certain embodiments, the β-catenin nucleic acid inhibitor molecules of the invention are dsRNAi inhibitor molecules where the antisense strand is between 18 and 66 nucleotides in length. Typically, the antisense strand comprises a sequence that is sufficiently complementary to a sequence in the target gene mRNA to direct the effect of the nucleic acid inhibitor molecule to the target gene. In certain embodiments, the antisense strand comprises a sequence that is fully complementary with a sequence contained in the target gene mRNA where the fully complementary sequence is between 18 and 40 nucleotides long. In certain of those embodiments, the antisense strand is between 20 and 50 nucleotides in length. In certain embodiments, the antisense strand is between 20 and 30 nucleotides in length. In certain embodiments, the antisense strand is 21, 22, 23, 24, 25, 26, 27, or 28 nucleotides in length. In certain embodiments, the antisense strand is between 35 and 40 nucleotides in length. In certain of those embodiments, the antisense strand is 36, 37, 38, or 39 nucleotides in length.

In certain embodiments, the β-catenin nucleic acid inhibitor molecule is a dsRNAi inhibitor molecule comprising a sense and an antisense strand and a duplex region of between 18 and 34 nucleotides, wherein the sense strand is 25-34 nucleotides in length and the antisense strand is 26-38 nucleotides in length and comprises 1-5 single-stranded nucleotides at its 3' terminus. In certain embodiments, the antisense strand comprises 2 single-stranded nucleotides at its 3' terminus. In certain embodiments, the antisense strand comprises 1-5 single-stranded nucleotides at its 3' terminus and 5-12 single-stranded nucleotides at is 5' terminus. In certain embodiments, the antisense strand comprises 2 single-stranded nucleotides at its 3' terminus and 10 single-stranded nucleotides at is 5' terminus.

In certain embodiments, the β-catenin nucleic acid inhibitor molecule is a dsRNAi inhibitor molecule comprising a sense and an antisense strand and a duplex region of 26 nucleotides, wherein the sense strand is 26 nucleotides in length and the antisense strand is 38 nucleotides in length and comprises 2 single-stranded nucleotides at its 3' terminus and 10 single-stranded nucleotides at its 5' terminus.

In certain embodiments, the β-catenin nucleic acid inhibitor molecules of the invention are ssRNAi inhibitor molecules.

In certain embodiments, the antisense strand of the β-catenin nucleic acid inhibitor molecule comprises the sequence of SEQ ID NO: 2. In certain embodiments, the antisense strand of the β-catenin nucleic acid inhibitor molecule consists of the sequence of SEQ ID NO: 2. In certain embodiments, the β-catenin nucleic acid inhibitor molecule is a dsRNAi inhibitor molecule and the sense strand comprises the sequence of SEQ ID NO: 1. In certain embodiments, the β-catenin nucleic acid inhibitor molecule is a dsRNAi inhibitor molecule and the sense strand consists of the sequence of SEQ ID NO: 1. In certain embodiments, the β-catenin nucleic acid inhibitor molecule is a dsRNAi inhibitor molecule and the sense strand comprises the sequence of SEQ ID NO: 1 and the antisense strand comprises the sequence of SEQ ID NO: 2. In certain embodiments, the β-catenin nucleic acid inhibitor molecule is a dsRNAi inhibitor molecule where the sense strand consists of the sequence of SEQ ID NO: 1 and the antisense strand consists of the sequence of SEQ ID NO: 2.

The level or activity of a β-catenin RNA can be determined by a suitable method now known in the art or that is later developed. It can be appreciated that the method used to measure a target RNA and/or the "expression" of a target gene can depend upon the nature of the target gene and its encoded RNA. For example, where the target β-catenin RNA sequence encodes a protein, the term "expression" can refer to a protein or the β-catenin RNA/transcript derived from the β-catenin gene (either genomic or of exogenous origin). In such instances the expression of the target β-catenin RNA can be determined by measuring the amount of β-catenin RNA/transcript directly or by measuring the amount of β-catenin protein. Protein can be measured in protein assays such as by staining or immunoblotting or, if the protein catalyzes a reaction that can be measured, by measuring reaction rates. All such methods are known in the art and can be used. Where target β-catenin RNA levels are to be measured, art-recognized methods for detecting RNA levels can be used (e.g., RT-PCR, Northern Blotting, etc.). In targeting β-catenin RNAs, it is also anticipated that measurement of the efficacy of the nucleic acid inhibitor molecule in reducing levels of β-catenin RNA or protein in a subject, tissue, in cells, either in vitro or in vivo, or in cell extracts can also be used to determine the extent of reduction of β-catenin-associated phenotypes (e.g., disease or disorders, e.g., cancer or tumor formation, growth, metastasis, spread, etc.). The above measurements can be made on cells, cell extracts, tissues, tissue extracts or other suitable source material.

MEK Inhibitors

As herein described, the term "MEK" refers to the mitogen-activated protein kinase kinase enzymes MEK1 and/or MEK2. MEK is also known as MAP2K and MAPKK. MEK is a member of the RAS/RAF/MEK/ERK signaling cascade that is activated in certain cancers, such as melanoma. The pathway is activated through the binding of a number of growth factors and cytokines to receptors on the cell surface, which activate receptor tyrosine kinases. Activation of the receptor tyrosine kinases results in activation of RAS, which then recruits RAF, which is in turn activated by multiple phosphorylation events.

Activated RAF phosphorylates and activates MEK kinase, which in turn phosphorylates and activates ERK kinase (also known as mitogen-activated protein kinase "MAPK"). The phosphorylated ERK can then translocate to the nucleus, where it phosphorylates and activates directly or indirectly various transcription factors, such as c-Myc and CREB. This process leads to altered gene transcription of genes that are important for cellular growth and proliferation.

As links in the RAS/RAF/MEK/ERK signaling cascade, MEK1 and MEK2 play crucial roles in tumorigenesis, cell proliferation, and inhibition of apoptosis. Although MEK1/2 are themselves rarely mutated, constitutively active MEK has been found in more than 30% of primary tumor cell lines tested. One of the ways of halting this cascade is the inhibition of MEK. When MEK is inhibited, cell proliferation is blocked and apoptosis is induced. Inhibition of MEK has, therefore, been an attractive target for development of pharmaceutical therapies.

MEK inhibitors include, but are not limited to, trametinib (GSK1120212), selumetinib, binimetinib (MEK162), cobimetinib (XL518), refametinib (BAY 86-9766), pimasertib, PD-325901, RO5068760, CI-1040 (PD035901), AZD8330 (ARRY-424704), RO4987655 (CH4987655), RO5126766, WX-554, E6201, and TAK-733. In one embodiment, the MEK inhibitor is trametinib.

Trametinib is a small molecule kinase inhibitor and is approved for use as a single agent or in combination with dabrafenib for the treatment of subjects with unresectable or metastatic melanoma with a V600E or V600K mutation in the BRAF gene. BRAF encodes a serine/threonine kinase called B-Raf that is involved in intracellular signaling.

c-Myc Nucleic Acid Inhibitor Molecules

The c-Myc gene is a key molecular regulator of cellular growth and differentiation. The c-Myc protein is a transcription factor that activates expression of many genes via binding of consensus sequences (Enhancer Box sequences (E-boxes)) and recruitment of histone acetyltransferases (HATs). The c-Myc protein can also act as a transcriptional repressor. By binding Miz-1 transcription factor and displacing the p300 co-activator, Myc inhibits expression of Miz-1 target genes. In addition, Myc has a direct role in the control of DNA replication (Dominguez-Sola et al. Nature 448 (7152): 445-51).

Various mitogenic signaling pathways, including Wnt, Shh and EGF (via the RAS/RAF/MEK/ERK pathway), have been demonstrated to activate c-Myc. The role of c-Myc in modifying the expression of its target genes has been shown to cause numerous biological effects. The first to be discovered was its capability to drive cell proliferation (upregulates cyclins, downregulates p21), but c-Myc also plays an important role in regulating cell growth (upregulates ribosomal RNA and proteins), apoptosis (downregulates Bcl-2), differentiation and stem cell self-renewal. c-Myc is a strong proto-oncogene and its upregulation has been described in many types of cancers. c-Myc overexpression stimulates gene amplification (Denis et al. Oncogene 6 (8): 1453-7), via a mechanism believed to involve DNA over-replication.

As disclosed herein β-catenin nucleic acid inhibitor molecules can be combined with c-Myc nucleic acid inhibitor molecules. As discussed above, various oligonucleotide structures have been used as nucleic acid inhibitor molecules and are known in the art. Specific c-Myc nucleic acid inhibitor molecules are known, as disclosed for example in U.S. Published Application Nos. 2014/0107178 and 2009/0099115, which are incorporated by reference for their disclosure of these c-Myc nucleic acid inhibitor molecules.

In certain embodiments, the c-Myc nucleic acid inhibitor molecule is a molecule disclosed in U.S. Published Application No. 2014/0107178.

In certain embodiments, the c-Myc nucleic acid inhibitor molecules of the invention are dsRNAi inhibitor molecules where the double-stranded region of the molecule is between 15 and 40 nucleotides in length. In certain of those embodiments, the double-stranded region is between 20 and 30 nucleotides in length. In certain of those embodiments, the double-stranded region is 21, 22, 23, 24, 25, or 26 nucleotides in length.

In certain embodiments, the c-Myc nucleic acid inhibitor molecules of the invention are dsRNAi inhibitor molecules where the sense strand is between 18 and 66 nucleotides in length. In certain of those embodiments, the sense strand is between 25 and 45 nucleotides in length. In certain embodiments, the sense strand is between 30 and 40 nucleotides in length. In certain embodiments, the sense strand is 36, 37, 38, 39, or 40 nucleotides in length. In certain embodiments, the sense strand is between 25 and 30 nucleotides in length. In certain of those embodiments, the sense strand is 25, 26, or 27 nucleotides in length.

In certain embodiments, the c-Myc nucleic acid inhibitor molecules of the invention are dsRNAi inhibitor molecules where the antisense strand is between 18 and 66 nucleotides in length. Typically, the antisense strand comprises a sequence that is sufficiently complementary to a sequence in the target gene mRNA to direct the effect of the nucleic acid inhibitor molecule to the target gene. In certain embodiments, the antisense strand comprises a sequence that is fully complementary with a sequence contained in the target gene mRNA where the fully complementary sequence is between 18 and 40 nucleotides long. In certain of those embodiments, the antisense strand is between 20 and 50 nucleotides in length. In certain embodiments, the antisense strand is between 20 and 30 nucleotides in length. In certain embodiments, the antisense strand is 21, 22, 23, 24, 25, 26, 27, or 28 nucleotides in length. In certain embodiments, the antisense strand is between 35 and 40 nucleotides in length. In certain of those embodiments, the antisense strand is 36, 37, 38, or 39 nucleotides in length.

In certain embodiments, the c-Myc nucleic acid inhibitor molecule is a dsRNAi inhibitor molecule comprising a sense and an antisense strand and a duplex region of between 18 and 40 nucleotides, wherein the sense strand is 25-34 nucleotides in length and the antisense strand is 26-38 nucleotides in length and comprises 1-5 single-stranded nucleotides at its 3' terminus. In certain embodiments, the antisense strand comprises 2 single-stranded nucleotides at its 3' terminus. In certain embodiments, the antisense strand comprises 1-5 single-stranded nucleotides at its 3' terminus and 5-12 single-stranded nucleotides at is 5' terminus. In certain embodiments, the antisense strand comprises 2 single-stranded nucleotides at its 3' terminus and 10 single-stranded nucleotides at is 5' terminus.

In certain embodiments, the c-Myc nucleic acid inhibitor molecule is a dsRNAi inhibitor molecule comprising a sense and an antisense strand and a duplex region of 26 nucleotides, wherein the sense strand is 26 nucleotides in length and the antisense strand is 38 nucleotides in length and comprises 2 single-stranded nucleotides at its 3' terminus and 10 single-stranded nucleotides at its 5' terminus. In certain embodiments, the c-Myc nucleic acid inhibitor molecule is a dsRNAi inhibitor molecule comprising a sense and an antisense strand and a duplex region of 25 nucleotides, wherein the sense strand is 25 nucleotides in length and the antisense strand is 27 nucleotides in length and comprises 2 single-stranded nucleotides at its 3' terminus.

In certain embodiments, the c-Myc nucleic acid inhibitor molecules of the invention are ssRNAi inhibitor molecules.

In certain embodiments, the antisense strand of the c-Myc nucleic acid inhibitor molecule comprises the sequence of SEQ ID NO: 4. In certain embodiments, the antisense strand of the c-Myc nucleic acid inhibitor molecule consists of the sequence of SEQ ID NO: 4. In certain embodiments, the c-Myc nucleic acid inhibitor molecule is a dsRNAi inhibitor molecule and the sense strand comprises the sequence of SEQ ID NO: 3. In certain embodiments, the c-Myc nucleic acid inhibitor molecule is a dsRNAi inhibitor molecule and the sense strand consists of the sequence of SEQ ID NO: 3. In certain embodiments, the c-Myc nucleic acid inhibitor molecule is a dsRNAi inhibitor molecule and the sense strand comprises the sequence of SEQ ID NO: 3 and the antisense strand comprises the sequence of SEQ ID NO: 4. In certain embodiments, the c-Myc nucleic acid inhibitor molecule is a dsRNAi inhibitor molecule where the sense strand consists of the sequence of SEQ ID NO: 3 and the antisense strand consists of the sequence of SEQ ID NO: 4. See FIG. 8.

In other embodiments, the antisense strand of the c-Myc nucleic acid inhibitor molecule comprises the sequence of SEQ ID NO: 6. In certain embodiments, the antisense strand of the c-Myc nucleic acid inhibitor molecule consists of the sequence of SEQ ID NO: 6. In certain embodiments, the c-Myc nucleic acid inhibitor molecule is a dsRNAi inhibitor molecule and the sense strand comprises the sequence of SEQ ID NO: 5. In certain embodiments, the c-Myc nucleic acid inhibitor molecule is a dsRNAi inhibitor molecule and the sense strand consists of the sequence of SEQ ID NO: 5. In certain embodiments, the c-Myc nucleic acid inhibitor molecule is a dsRNAi inhibitor molecule and the sense strand comprises the sequence of SEQ ID NO: 5 and the antisense strand comprises the sequence of SEQ ID NO: 6. In certain embodiments, the c-Myc nucleic acid inhibitor molecule is a dsRNAi inhibitor molecule and the sense strand consists of the sequence of SEQ ID NO: 5 and the antisense strand consists of the sequence of SEQ ID NO: 6. See FIG. 9.

In certain embodiments, a nucleic acid inhibitor molecule is conjugated to a ligand to direct delivery of the nucleic acid inhibitor molecule to the targeted tumor. Ligands that may be used include, but are not limited to, antibodies, peptides, small molecules, and carbohydrates. In certain embodiments, the ligand may be a folate, an RGD peptide, a PSMA binding ligand (see, e.g., WO 2010/045598), transferrin (see, e.g., Yhee et al. (2013), Bioconjugate Chem., 24, 1850-1860), or an aptamer (see, e.g., Dassie (2013), Ther Deliv, 4(12): 1527-1546).

In certain embodiments, a nucleic acid inhibitor molecule is covalently linked to a nucleic acid targeting molecule, such as a DNA or RNA aptamer, to achieve tumor targeting. In certain embodiments, a nucleic acid inhibitor molecule is linked to the targeting nucleic acid molecule by a nucleic acid linker. In certain embodiments, a strand of the nucleic acid inhibitor molecule and the targeting nucleic acid molecule comprise a continuous oligonucleotide. In some embodiments, the targeting nucleic acid molecule links the two strands of a dsRNAi inhibitor molecule.

The level or activity of a c-Myc RNA can be determined by a suitable method now known in the art or that is later developed. It can be appreciated that the method used to measure a target RNA and/or the "expression" of a target gene can depend upon the nature of the target gene and its encoded RNA. For example, where the target c-Myc RNA sequence encodes a protein, the term "expression" can refer to a protein or the c-Myc RNA/transcript derived from the c-Myc gene (either genomic or of exogenous origin). In such instances the expression of the target c-Myc RNA can be determined by measuring the amount of c-Myc RNA/transcript directly or by measuring the amount of c-Myc protein. Protein can be measured in protein assays such as by staining or immunoblotting or, if the protein catalyzes a reaction that can be measured, by measuring reaction rates. All such methods are known in the art and can be used. Where target c-Myc RNA levels are to be measured, art-recognized methods for detecting RNA levels can be used (e.g., RT-PCR, Northern Blotting, etc.). In targeting c-Myc RNAs, it is also anticipated that measurement of the efficacy of the nucleic acid inhibitor molecule in reducing levels of c-Myc RNA or protein in a subject, tissue, in cells, either in vitro or in vivo, or in cell extracts can also be used to determine the extent of reduction of c-Myc-associated phenotypes (e.g., disease or disorders, e.g., cancer or tumor formation, growth, metastasis, spread, etc.). The above measurements can be made on cells, cell extracts, tissues, tissue extracts or other suitable source material.

Pharmaceutical Compositions

The present disclosure provides pharmaceutical compositions comprising a β-catenin nucleic acid inhibitor molecule and a pharmaceutically acceptable excipient. In certain embodiments, the pharmaceutical composition comprising the β-catenin nucleic acid inhibitor molecule and the pharmaceutically acceptable excipient further comprises a MEK inhibitor or a nucleic acid inhibitor molecule that reduces expression of the c-Myc gene.

The pharmaceutically acceptable excipients useful in this disclosure are conventional. Remington's Pharmaceutical Sciences, by E. W. Martin, Mack Publishing Co., Easton, Pa., 15$^{th}$ Edition (1975), describes compositions and formulations suitable for pharmaceutical delivery of one or more therapeutic compositions, including vaccines, and additional pharmaceutical agents. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In general, the nature of the excipient will depend on the particular mode of administration being employed. For instance, parenteral formulations usually comprise injectable fluids that include pharmaceutically and physiologically acceptable fluids such as water, physiological saline, balanced salt solutions, buffers, aqueous dextrose, glycerol or the like as a vehicle. For solid compositions (for example, powder, pill, tablet, or capsule forms), conventional non-toxic solid excipients can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, a surface active agent, preservatives, and pH buffering agents and the like, for example sodium acetate or sorbitan monolaurate. In certain embodiments, the pharmaceutically acceptable excipient is non-naturally occurring.

The pharmaceutical composition according to certain embodiments disclosed herein, may comprise at least one ingredient, which may belong to the same or different categories of excipients, including at least one disintegrant, at least one diluent, and/or at least one binder.

Typical non-limiting examples of the at least one disintegrant that may be added to the pharmaceutical composition according to embodiments disclosed herein, include, but are not limited to, povidone, crospovidone, carboxymethylcellulose, methylcellulose, alginic acid, croscarmellose sodium, sodium starch glycolate, starch, formaldehyde-casein, and combinations thereof.

Typical non-limiting examples of the at least one diluents that may be added to the pharmaceutical composition according to embodiments disclosed herein, include, but are not limited to, maltose, maltodextrin, lactose, fructose, dextrin, microcrystalline cellulose, pregelatinized starch, sorbitol, sucrose, silicified microcrystalline cellulose, powdered cellulose, dextrates, mannitol, calcium phosphate, and combinations thereof.

Typical non-limiting examples of the at least one binder that may be added to the pharmaceutical composition according to embodiments disclosed herein, include, but are not limited to, acacia, dextrin, starch, povidone, carboxymethylcellulose, guar gum, glucose, hydroxypropyl methylcellulose, methylcellulose, polymethacrylates, maltodextrin, hydroxyethyl cellulose, and combinations thereof.

Suitable preparation forms for the pharmaceutical compositions disclosed herein include, for example, tablets, capsules, soft capsules, granules, powders, suspensions, aerosols, emulsions, microemulsions, nanoemulsions, unit dosage forms, rings, films, suppositories, solutions, creams, syrups, transdermal patches, ointments, or gels.

The β-catenin nucleic acid inhibitor molecule and/or the c-Myc nucleic acid inhibitor molecule may be admixed, encapsulated, conjugated or otherwise associated with other molecules, molecule structures or mixtures of compounds, including, for example, liposomes and lipids such as those disclosed in U.S. Pat. Nos. 6,815,432, 6,586,410, 6,858,225, 7,811,602, 7,244,448 and 8,158,601; polymeric materials such as those disclosed in U.S. Pat. Nos. 6,835,393, 7,374,778, 7,737,108, 7,718,193, 8,137,695 and U.S. Published Patent Application Nos. 2011/0143434, 2011/0129921, 2011/0123636, 2011/0143435, 2011/0142951, 2012/0021514, 2011/0281934, 2011/0286957 and 2008/0152661; capsids, capsoids, or receptor targeted molecules for assisting in uptake, distribution or absorption.

In certain embodiments, the nucleic acid inhibitor molecules are formulated in a lipid nanoparticle. Lipid-nucleic acid nanoparticles typically form spontaneously upon mixing lipids with nucleic acid to form a complex. Depending on the desired particle size distribution, the resultant nanoparticle mixture can be optionally extruded through a polycarbonate membrane (e.g., 100 nm cut-off) using, for example, a thermobarrel extruder, such as Lipex Extruder (Northern Lipids, Inc). To prepare a lipid nanoparticle for therapeutic use, it may be desirable to remove solvent (e.g., ethanol) used to form the nanoparticle and/or exchange buffer, which can be accomplished by, for example, dialysis or tangential flow filtration. Methods of making lipid nanoparticles containing nucleic acid inhibitor molecules are known in the art, as disclosed, for example in U.S. Published Patent Application Nos. 2015/0374842 and 2014/0107178.

In certain embodiments, the LNP comprises a liposome comprising a cationic liposome and a pegylated lipid. The LNP can further comprise one or more envelope lipids, such as a cationic lipid, a structural lipid, a sterol, a pegylated lipid, or mixtures thereof.

Cationic lipids for use in LNPs are known in the art, as discussed for example in U.S. Published Patent Application Nos. 2015/0374842 and 2014/0107178. Typically, the cationic lipid is a lipid having a net positive charge at physiological pH. In certain embodiments, the cationic liposome is DODMA, DOTMA, DL-048, or DL-103. In certain embodiments the structural lipid is DSPC, DPPC or DOPC. In certain embodiments, the sterol is cholesterol. In certain embodiments, the pegylated lipid is DMPE-PEG, DSPE-PEG, DSG-PEG, DMPE-PEG2K, DSPE-PEG2K, DSG-PEG2K, or DSG-MPEG. In one embodiment, the cationic lipid is DL-048, the pegylated lipid is DSG-MPEG and the one or more envelope lipids are DL-103, DSPC, cholesterol, and DSPE-MPEG.

These pharmaceutical compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above mentioned agent or agents, such as in a sealed package of tablets or capsules. The composition in solid form can also be packaged in a container for a flexible quantity, such as in a squeezable tube designed for a topically applicable cream or ointment.

In certain embodiments, the pharmaceutical compositions described herein are for use in treating a β-catenin-associated disease or disorder. In certain embodiments, the pharmaceutical composition for use in treating a β-catenin-associated disease or disorder comprises a β-catenin nucleic acid inhibitor molecule, wherein the composition is administered in combination with a MEK inhibitor (e.g., trametinib). In other embodiments, the pharmaceutical composition for use in treating a β-catenin-associated disease or disorder comprises a β-catenin nucleic acid inhibitor molecule, wherein the composition is administered in combination with a c-Myc nucleic acid inhibitor molecule. In certain embodiments, the β-catenin-associated disease or disorder is cancer, such as colorectal cancer, hepatocellular carcinoma, or melanoma. In certain embodiments, the β-catenin-associated cancer has metastasized. In certain embodiments, the β-catenin-associated cancer is colorectal cancer that has metastasized. In certain embodiments, the colorectal cancer has metastasized to the liver.

Methods of Administration/Treatment

Typically, the nucleic acid inhibitor molecules of the invention are administered intravenously or subcutaneously. However, the pharmaceutical compositions disclosed herein may also be administered by any method known in the art, including, for example, oral, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like. Administration may also be via injection, for example, intraperitoneally, intramuscularly, intradermally, intraorbitally, intracapsularly, intraspinally, intrasternally, or the like.

The therapeutically effective amount of the compounds disclosed herein may depend on the route of administration and the physical characteristics of the patient, such as general state, weight, diet, and other medications. As used herein, a therapeutically effective amount means an amount of compound or compounds effective to prevent, alleviate or ameliorate disease or condition symptoms of the subject being treated. Determination of a therapeutically effective amount is well within the capability of those skilled in the art and generally range from about 0.5 mg to about 3000 mg of the small molecule agent or agents per dose per patient.

In one aspect, the pharmaceutical compositions disclosed herein may be useful for the treatment or prevention of symptoms related to a β-catenin-associated disease or disorder. One embodiment is directed to a method of treating a β-catenin-associated disease or disorder, comprising administering to a subject a therapeutically effective amount of a β-catenin nucleic acid inhibitor molecule and a therapeutically effective amount of an MEK inhibitor. Another embodiment is directed to a method of treating a β-catenin-associated disease or disorder, comprising administering to a subject a therapeutically effective amount of a β-catenin nucleic acid inhibitor molecule and a therapeutically effective amount of a c-Myc nucleic acid inhibitor molecule.

Typically, the nucleic acid inhibitor molecule is administered separately from, and on a different schedule than, a small molecule therapeutic that is in combination with the nucleic acid inhibitor molecule. For example, when used as a single agent, trametinib is currently prescribed as a daily oral dose (typically about 1-2 mg/day). The nucleic acid inhibitor molecule, on the other hand, is likely to be administered through an intravenous or subcutaneous route with doses given once a week, once each two weeks, once a month, once every three months, twice a year, etc. The subject may already be taking the small molecule therapeutic at the initiation of the administration of the nucleic acid inhibitor molecule. In other embodiments, the subject may begin administration of both the small molecule therapeutic and the nucleic acid inhibitor molecule at about the same time. In other embodiments, the subject may begin taking the small molecule therapeutic after the initiation of administration of the nucleic acid inhibitor molecule.

In certain embodiments for the methods of treatment disclosed herein, one pharmaceutical composition may comprise the β-catenin nucleic acid inhibitor molecule and a separate pharmaceutical composition may comprise the MEK inhibitor or the c-Myc nucleic acid inhibitor molecule.

In other embodiments, the β-catenin nucleic acid inhibitor molecule may be administered simultaneously with the MEK inhibitor or the c-Myc nucleic acid inhibitor molecule.

Accordingly, in certain embodiments for the methods of treatment disclosed herein, a single pharmaceutical composition may comprise both the β-catenin nucleic acid inhibitor molecule and the MEK inhibitor or the c-Myc nucleic acid inhibitor molecule. Thus, in one embodiment of the treatment methods disclosed herein, a single pharmaceutical composition is administered to the subject, wherein the single pharmaceutical composition comprises both the β-catenin nucleic acid inhibitor molecule and the MEK inhibitor, such as trametinib. In another embodiment of the treatment methods disclosed herein, the single pharmaceutical composition comprises both the β-catenin nucleic acid inhibitor molecule and the c-Myc nucleic acid inhibitor molecule.

In certain embodiments, the β-catenin nucleic acid inhibitor molecule or c-Myc nucleic acid inhibitor molecule is administered at a dosage of 20 micrograms to 10 milligrams per kilogram body weight of the recipient per day, 100 micrograms to 5 milligrams per kilogram, 0.25 milligrams to 2.0 milligrams per kilogram, or 0.5 to 2.0 milligrams per kilogram.

In certain embodiments, the β-catenin nucleic acid inhibitor molecule or c-Myc nucleic acid inhibitor molecule is administered once daily, once weekly, once every two weeks, once monthly, once every two months, once a quarter, twice a year, or once yearly. In certain embodiments, the β-catenin nucleic acid inhibitor molecule or c-Myc nucleic acid inhibitor molecule is administered once or twice every 2, 3, 4, 5, 6, or 7 days. The compositions (containing both agents or a single, individual agent) can be administered once monthly, once weekly, once daily (QD), once every other day, or divided into multiple monthly, weekly, or daily doses, such as twice daily, three times a day or once every two weeks. In certain embodiments, the compositions can be administered once a day for two, three, four, five, six, or at least seven days. Although the agents can be administered simultaneously, typically each agent will be administered on a different schedule, particularly if the agents are administered via different routes.

Alternatively, continuous intravenous infusion sufficient to maintain therapeutically effective concentrations in the blood are contemplated. The skilled artisan will appreciate that certain factors may influence the dosage and timing required to effectively treat a subject, including but not limited to the severity of the disease or disorder, previous treatments, the general health and/or age or weight of the subject, and other diseases present.

Treatment of a subject with a therapeutically effective amount of an agent can include a single treatment or, preferably, can include a series of treatments. In certain embodiments, the treatment schedule includes a first loading dosage or phase, which is typically a higher dosage or frequency, followed by a maintenance dosage or phase, which is typically a lower dosage or frequency than the loading dosage/phase. Typically, the treatment continues until disease progression or unacceptable toxicity occurs.

In certain embodiments, the β-catenin or c-Myc nucleic acid inhibitor molecules can be inserted into expression constructs, e.g., viral vectors, retroviral vectors, expression cassettes, or plasmid viral vectors, e.g., using methods known in the art. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057).

The expression constructs may be constructs suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, e.g., Tuschl (2002, Nature Biotechnol 20: 500-505).

One aspect is directed to methods of treating a β-catenin-associated disease or disorder, comprising administering to a subject (preferably a human) a therapeutically effective amount of a β-catenin nucleic acid inhibitor molecule and a therapeutically effective amount of an MEK inhibitor or a c-Myc nucleic acid inhibitor molecule.

In one embodiment, the β-catenin nucleic acid inhibitor molecule is a dsRNAi inhibitor molecule. In certain of those embodiments, the sense strand comprises or consists of the sequence of SEQ ID NO: 1 and the antisense strand comprises of comprises or consists of the sequence of SEQ ID NO: 2. In one embodiment the β-catenin nucleic acid inhibitor molecule is formulated with a lipid nanoparticle. In one embodiment, the β-catenin nucleic acid inhibitor molecule is administered intravenously.

In one embodiment, the method of treatment comprises administering to a subject (preferably a human) a therapeutically effective amount of a β-catenin nucleic acid inhibitor molecule and a therapeutically effective amount of an MEK inhibitor. In one embodiment, the MEK inhibitor is trametinib. In one embodiment, the trametinib is administered orally. In one embodiment, trametinib is administered at a dosage of about 1-2 mg daily or every other day. In one embodiment, trametinib is administered at a dosage of 2 mg daily.

In one embodiment, the MEK inhibitor is trametinib, which is administered orally, and the β-catenin nucleic acid inhibitor molecule is a dsRNAi inhibitor molecule, wherein the double-stranded region of the molecule is between 15 and 40 nucleotides in length, including, for example, a double stranded nucleic acid having a sense strand and an antisense strand, wherein the sense strand comprises or consists of the sequence of SEQ ID NO: 1 and the antisense strand comprises of consists of the sequence of SEQ ID NO: 2. The β-catenin dsRNAi inhibitor molecule can be formulated with a lipid nanoparticle and administered intravenously.

In another embodiment, the method of treatment comprises administering to a subject (preferably a human) a therapeutically effective amount of a β-catenin nucleic acid inhibitor molecule and a therapeutically effective amount of a c-Myc nucleic acid inhibitor molecule.

In one embodiment, the c-Myc nucleic acid inhibitor molecule is a dsRNAi inhibitor molecule. In certain of those embodiments, the sense strand comprises or consists of the sequence of SEQ ID NO: 3 and the antisense strand comprises of consists of the sequence of SEQ ID NO: 4. In another embodiment, the sense strand comprises or consists of the sequence of SEQ ID NO: 5 and the antisense strand comprises of consists of the sequence of SEQ ID NO: 6. In one embodiment the c-Myc dsRNAi inhibitor molecule is formulated with a lipid nanoparticle. In one embodiment, the c-Myc dsRNAi inhibitor molecule is administered intravenously.

In certain embodiments of these treatment methods, the β-catenin-associated disease or disorder is cancer, such as colorectal cancer, hepatocellular carcinoma, or melanoma, and the subject has a mutation in the β-catenin gene. In other embodiments, the subject has colorectal cancer characterized by a mutation in the β-catenin gene (or another gene in the Wnt signaling pathway, such as APC) and the KRAS gene. In certain embodiments the subject has a BRAF mutation. In certain embodiments, the subject has a BRAF mutation and a mutation in a gene that encodes a protein involved in the Wnt signaling pathway (e.g., APC). In certain embodiments where trametinib is administered as an MEK inhibitor, the subject has a BRAF mutation (e.g., V600E or V600F). In certain embodiments, the subject with the BRAF mutation has melanoma.

In certain embodiments of these treatment methods, the β-catenin-associated cancer has metastasized. In certain embodiments, the β-catenin-associated cancer is colorectal cancer that has metastasized. In certain embodiments, the colorectal cancer has metastasized to the liver. In certain embodiments, the treatment reduces metastases, including, but not limited to, metastases in the liver, in the subject. In certain embodiments, the treatment with the combination of a β-catenin nucleic acid inhibitor molecule, such as a dsRNAi inhibitor molecule, and an MEK inhibitor, such as trametinib, increases survival of the subject beyond the average survival of patients with metastasized cancer who receive treatment with either the β-catenin nucleic acid inhibitor molecule or the MEK inhibitor (individually rather than in combination).

EXAMPLES

Example 1: BCAT1 Construct

A nucleic acid inhibitor molecule that targets the β-catenin gene was constructed ("BCAT1"). BCAT1 has a 26 base pair passenger strand and a 38 base pair guide strand that form a duplex region consisting of 26 base pairs. FIG. 7. The 5' end of the passenger strand consists of a 10-base pair, single stranded overhang, and the 3' end of the guide strand consists of a two-base pair single-stranded, overhang. FIG. 7.

The BCAT1 construct was formulated in EnCore lipid nanoparticles (LNP). The LNP formulated BCAT1 effectively delivered the nucleic acid payload to multiple tumor types (see Table I below), including subcutaneous, orthotopic, disseminated and metastatic xenograft tumors, patient-derived xenografts (PDX), and genetically engineered models (GEM).

TABLE I

Delivery of BCAT1 to Various Tumor Types

| Tumor type | Description | Tumor location in model |
|---|---|---|
| Acute lymphoblastic leukemia | ALL697 | disseminated/spleen |
| Acute lymphoblastic leukemia | NALM-6 | disseminated/spleen |
| Acute myelogenous leukemia | KG1 | disseminated/spleen, liver |
| Colorectal | LS411N CLDX | metastases/liver, primary/spleen |
| Colorectal | SW403 CLDX | metastases/liver |
| Colorectal | LS174T CLDX | metastases/liver, primary/spleen |
| Colorectal | SW1116 CLDX | primary/spleen |
| Colorectal | LS411N CLDX | subcutaneous/flank |
| Colorectal | SW403 CLDX | subcutaneous/flank |
| Colorectal | LS174T CLDX | subcutaneous/flank |
| Colorectal | PDX | subcutaneous/flank |
| Hepatoblastoma | liver-specific GEMM/CTNNB1-YAP | spontaneous/liver |
| Hepatoblastoma | HepG2 CLDX | subcutaneous/flank |
| Hepatoblastoma | HepG2 CLDX | orthotopic/liver |
| Hepatocellular Carcinoma | Hep3B CLDX | subcutaneous/flank |
| Hepatocellular Carcinoma | Hep3B CLDX | orthotopic/liver |

TABLE I-continued

Delivery of BCAT1 to Various Tumor Types

| Tumor type | Description | Tumor location in model |
|---|---|---|
| Hepatocellular Carcinoma | PDX | orthotopic/liver |
| Hepatocellular Carcinoma | GEMM/Mst1 | spontaneous/liver |
| Hepatocellular Carcinoma | liver-specific GEMM/CTNNB1-KRAS | spontaneous/liver |
| Hepatocellular Carcinoma | liver-specific GEMM/Myc | spontaneous/liver |
| Lung | Lewis Lung Carcinoma | subcutaneous/flank |
| Melanoma | B16F10 CLDX | subcutaneous/flank |
| Melanoma | B16F10 CLDX | disseminated/lung, liver |
| Multiple Myeloma | KMS11 | subcutaneous/flank |
| NSCLC | PDX | subcutaneous/flank |
| Osteosarcoma | PDX | subcutaneous/flank |
| Ovarian | PDX | subcutaneous/flank |
| Pancreatic | MiaPaca2 | subcutaneous/flank |
| Pancreatic | PDX | subcutaneous/flank |
| Renal Cell Carcinoma | 786/0 | subcutaneous/flank |

Negative: HCT116, DLD1, HL60

Example 2: Tumor Studies 6-8 week old Hsd:Athymic Nude-Foxn1$^{nu}$ mice (hereby referred to as nude mice) were injected subcutaneously with LS411N ($5 \times 10^6$ cells), SW403 ($5 \times 10^6$ cells), Ls174t ($5 \times 10^6$ cells) or Hep3B ($5 \times 10^6$ cells+matrigel) under the right shoulder. Tumor volume was measured twice a week to monitor tumor growth/suppression. Dosing was initiated when the tumors reached 200-250 mm$^3$. For tumor growth inhibition studies, animals were randomized and assigned to different cohorts and subjected to dosing cycles. BCAT1 or LNP was given intravenously via lateral tail vein at a total volume of 10 ml/kg. Trametinib was given orally at a volume of 10 mi/kg.

Colorectal cancer (CRC) liver metastases models were generated by surgically implanting 1-2×10$^6$ cells in the spleen of nude mice after midline abdominal incision. After surgery, the abdominal incision was closed with 5-0 to 6-0 absorbable, nonbraided suture and the skin was closed with a single wound clip. Mice were anesthetized with isoflurane before initiating the surgery and during surgery. Buprenorphine was given preoperatively and post-operatively at 0.1 mg/kg subcutaneously for pain relief. Mice were held in a pathogen-free environment and all procedures involving animals were performed according to protocols approved by Dicerna Pharmaceuticals' Institutional Animal Care and Use Committee (Dicerna-IACUC).

Human cell lines LS411N and SW403, Ls174t and Hep3B were obtained from ATCC (Manassas, Va.) and grown in RPMI/DMEM medium supplemented with 10% FBS. LS411N is a human colorectal cell line harboring mutations in the adenomatous polyposis coli (APC) and BRAF genes. APC is a component of the destruction complex in the Wnt signaling pathway. See FIG. 1. SW403 is a human colorectal cell line harboring mutations in the APC and KRAS genes. Ls174t is a human colorectal cell line harboring mutations in the CTNNB1 and KRAS genes.

Example 3: BCAT1 Effective in Wnt Active Tumors

Figure 2A:
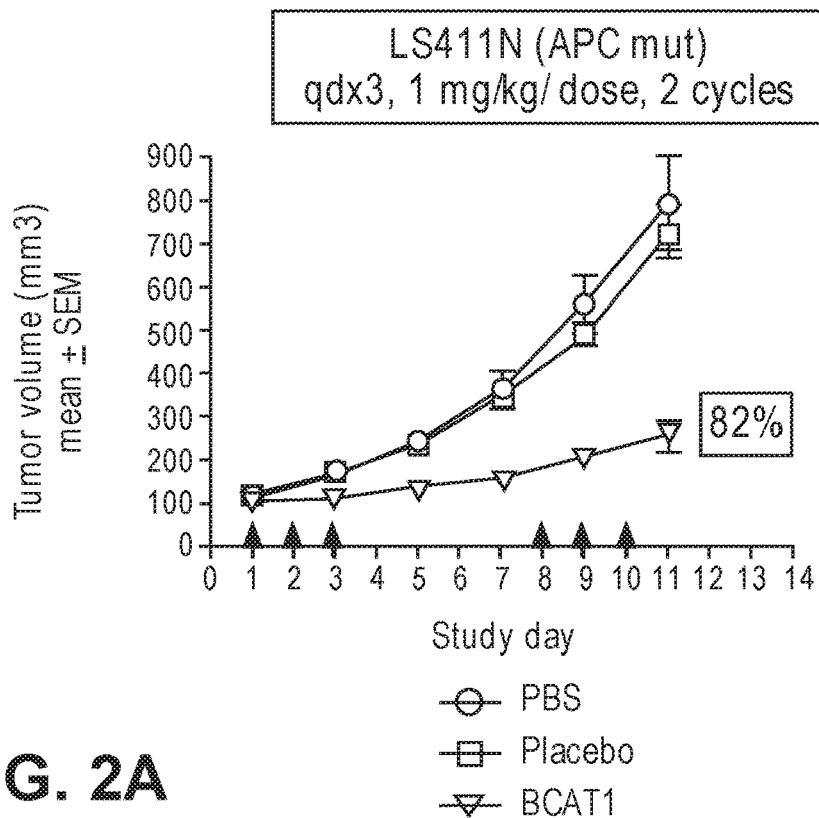
FIGS. 2A-D demonstrate BCAT1 anti-tumor efficacy at different dosages and frequency of administration in Wnt active LS411N tumors. BCAT1 was administered at 1.0 mg/kg, every day for 3 days (2 cycles) (FIG. 2A); 3 mg/kg, every week (2 cycles) (FIG. 2B); 0.3 mg/kg, every day for 3 days (2 cycles) (FIG. 2C); or 3 mg/kg, every day for 3 days (2 cycles) (FIG. 2D).
Figure 2B:
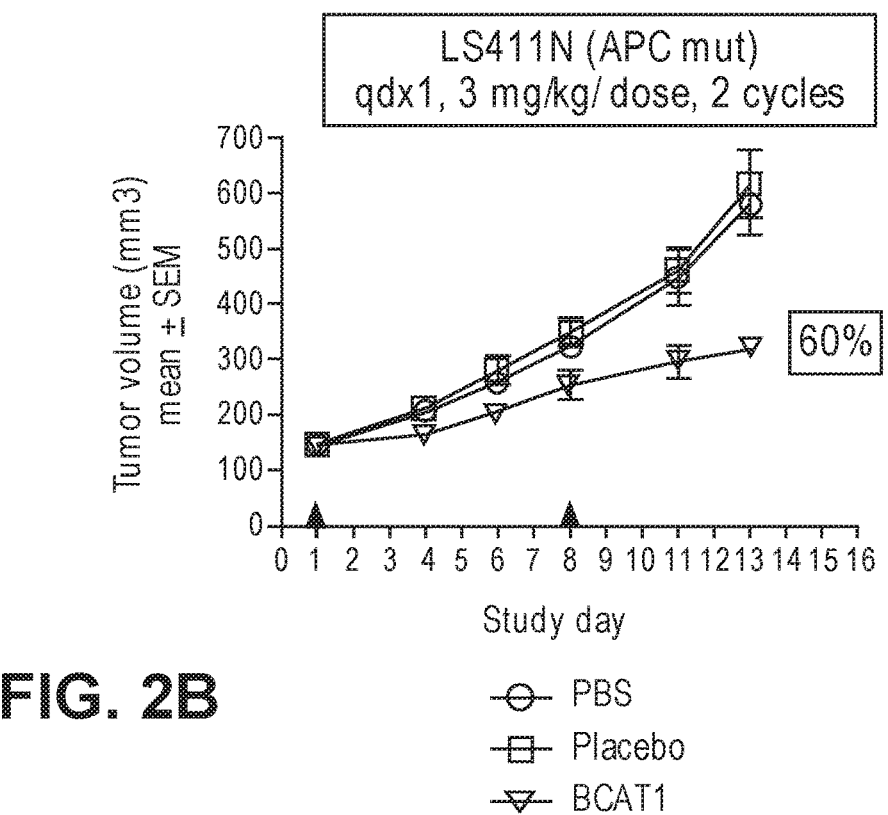
Figure 2C:
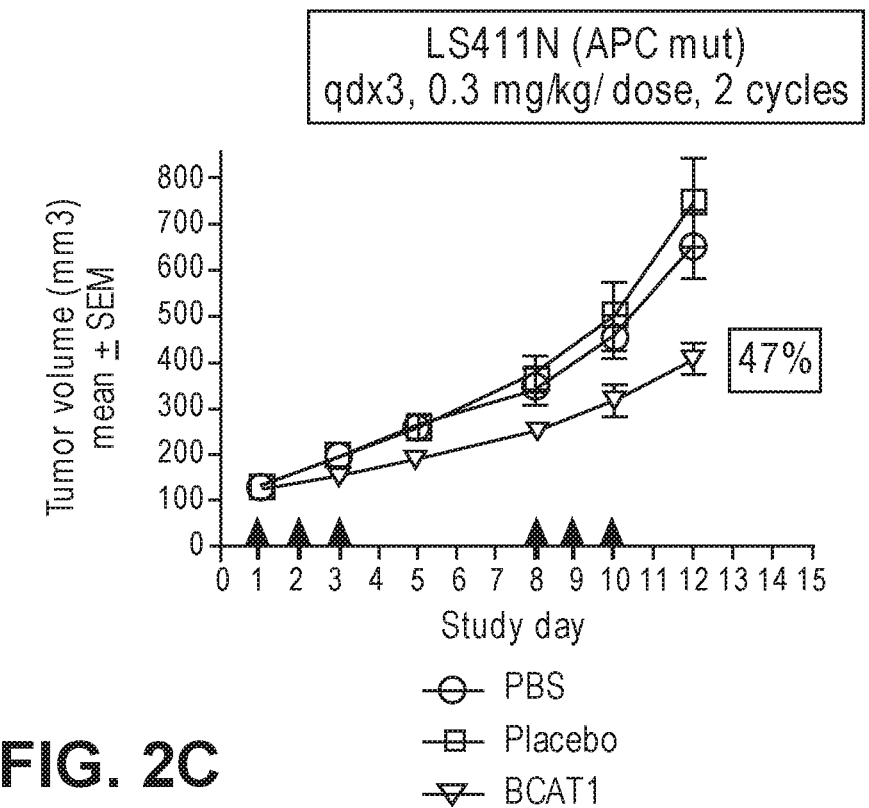
Figure 2D:
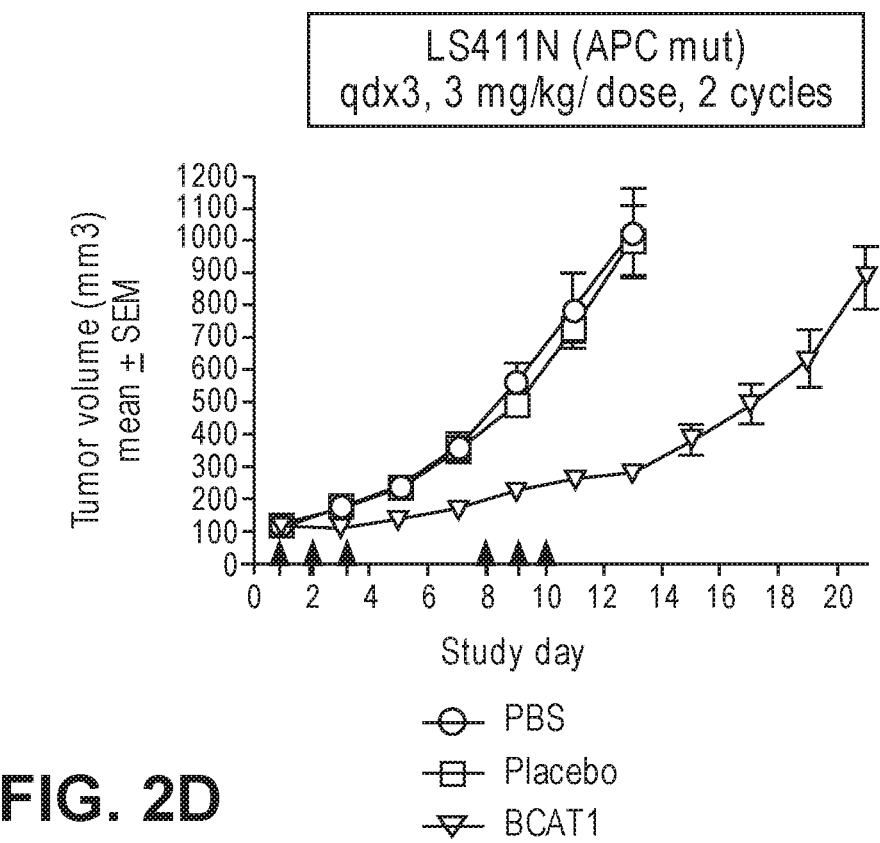

The single agent efficacy of BCAT1 was evaluated at different dose levels in different colorectal cancer models. After two weekly dosing cycles (qdx3, 1 mg/kg), BCAT1 caused tumor growth inhibition of 82% relative to vehicle-treated animals in LS411N tumors. FIG. 2A. When the dosing regimen was changed to a weekly dosing (qwx1, 3 mg/kg), the tumor growth inhibition dropped slightly to 60% (FIG. 2B), suggesting that a more vigorous dosing regimen is necessary to effectively treat these tumors. When the mice were treated at lower dose levels (qdx3, 0.3 mg/kg), the tumor growth inhibition was further reduced to 47%, demonstrating a nice dose response. FIG. 2C. In a cohort where therapy was discontinued after the second cycle (qdX3, 3 mg/kg), tumor growth resumed to a level roughly comparable to untreated subjects (FIG. 2D), suggesting that long-term suppression of β-catenin is required for maintenance of efficacy in this model. Without intending to be bound by any theory, it appears that the Wnt pathway may be reactivated when treatment is stopped.

Figure 3A:
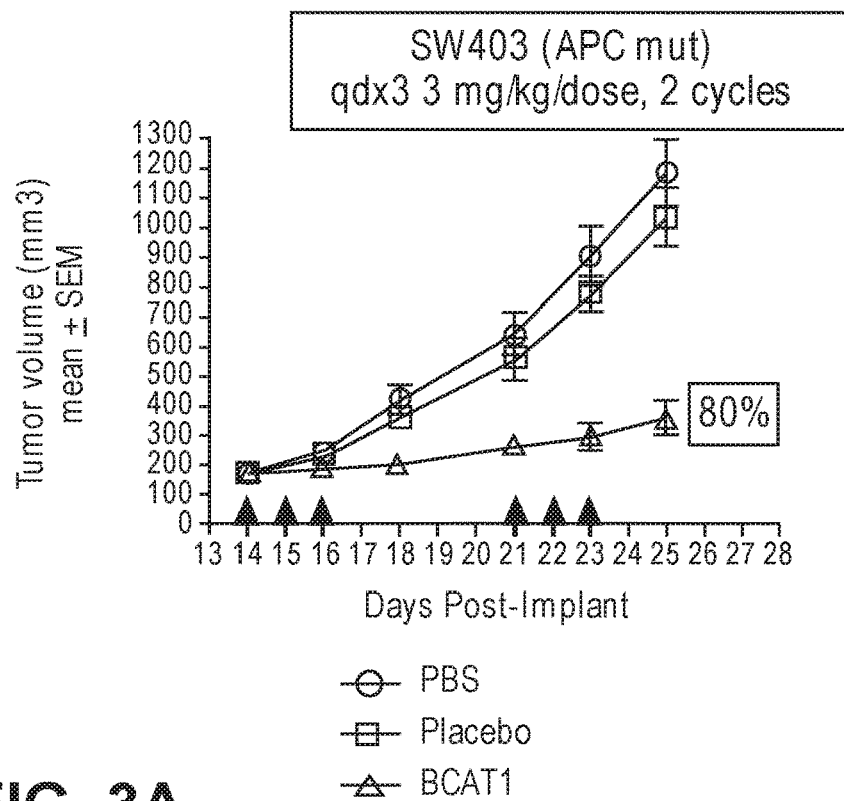
FIGS. 3A-C show that BCAT1 selectively targets Wnt signaling. Administration of BCAT1 effectively reduces tumor volume in the Wnt active tumor cells: SW403 (APC and KRAS mutations.
Figure 3B:
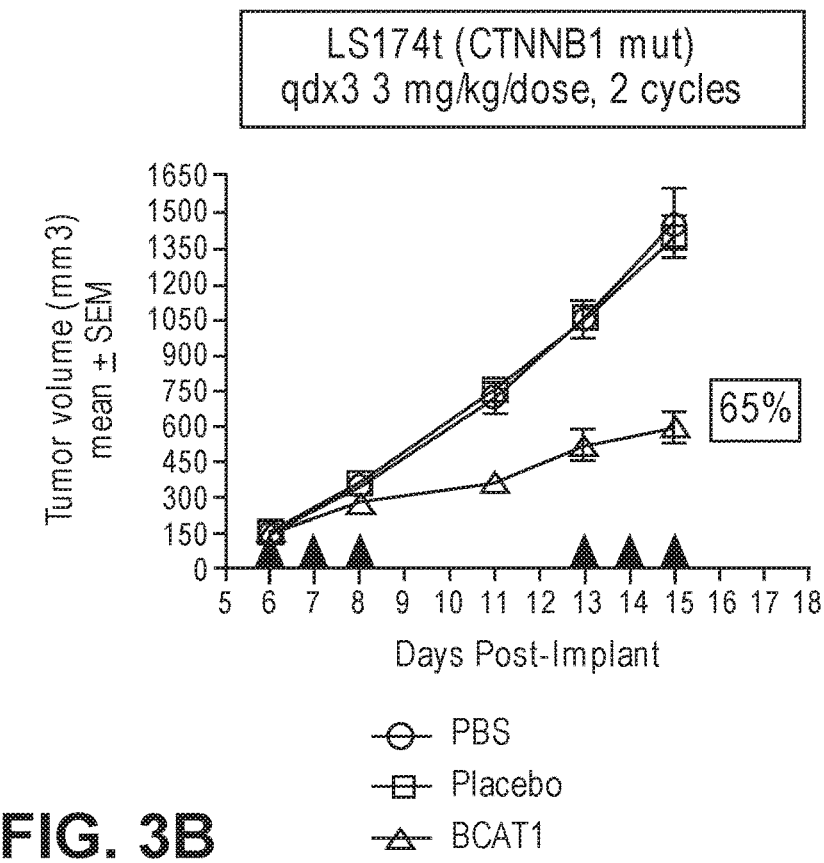
Figure 3C:
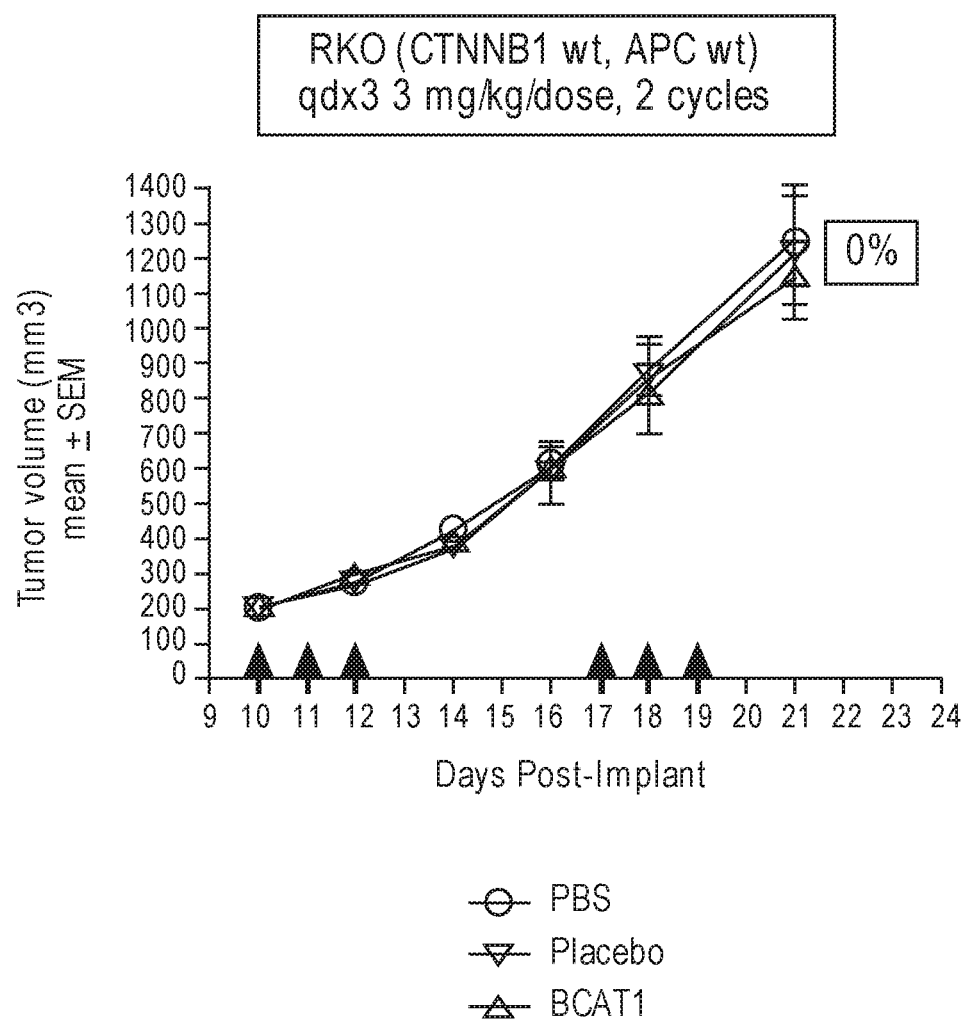

BCAT1 demonstrated robust efficacy in other CRC tumors with Wnt activation. Robust efficacy was also demonstrated in SW403 cells (FIG. 3A) and Ls174t cells (FIG. 3B) at qdx3, 3 mg/kg dose levels (2 cycles). No efficacy was observed in β-catenin/APC wild type RKO tumors (FIG. 3C) at the same dose levels, suggesting that the tumor growth inhibition requires activated Wnt signaling, confirming target dependence.

Example 4: Combination of BCAT1 and Trametinib Mediate Synergistic Efficacy

Combination therapy with BCAT1 and an MEK inhibitor (trametinib) was evaluated. Trametinib (99% purity) was dissolved in DMSO to make a clear solution of 5 mg/ml. This solution was diluted in a solvent mixture (10% Ethanol, 10% Cremophor, 80% water) to make different diluted versions. The vehicle used in the combination studies consists of 10% DMSO in PBS to match the DMSO concentration in the Trametinib doses.

Figure 4A:
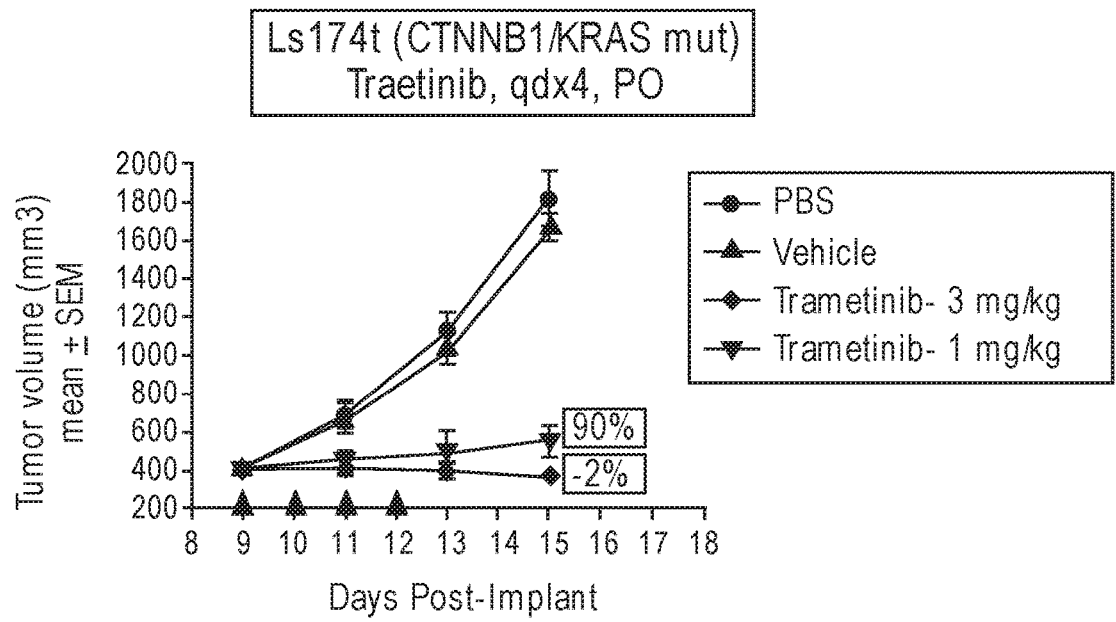
FIGS. 4A-B show that combination therapy with BCAT1 and a MEK inhibitor (trametinib) enhance the anti-tumor efficacy as compared to treatment with either of BCAT1 or trametinib individually.
Figure 4B:
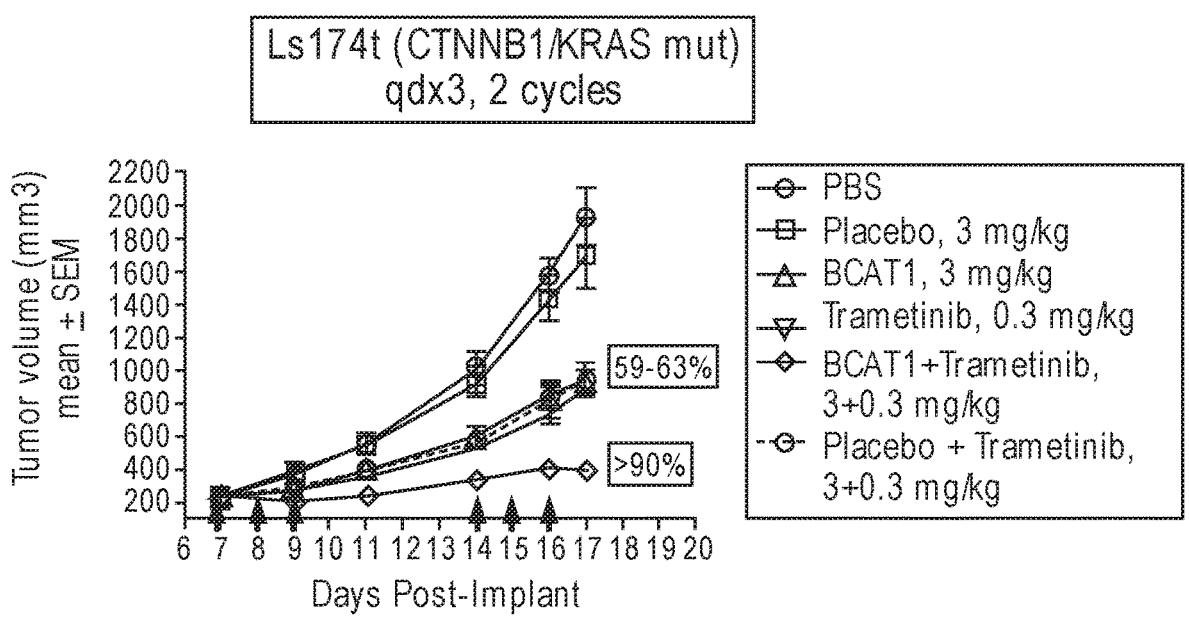
Figure 4C:
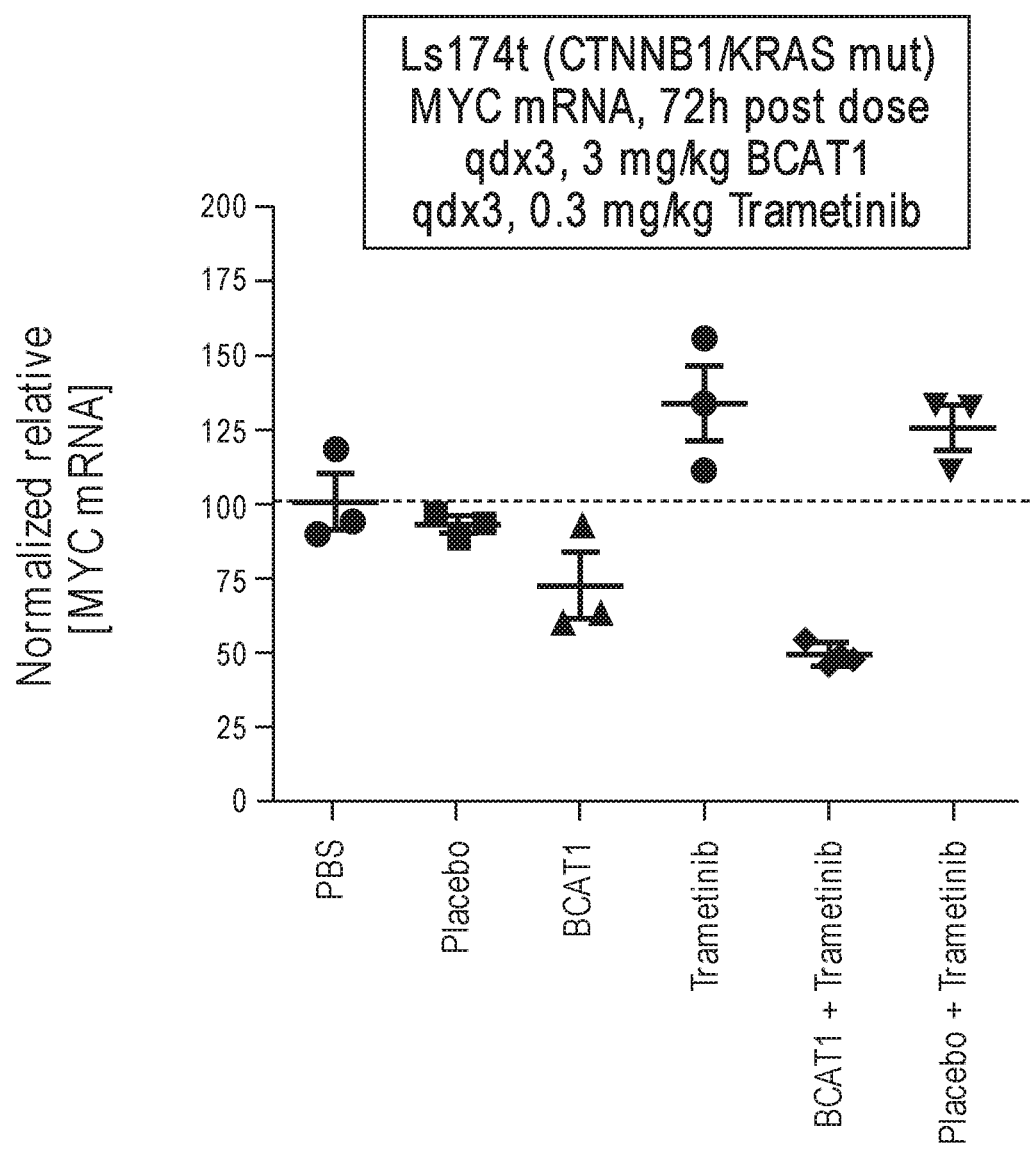
FIG. 4C shows that combination therapy with BCAT1 and a MEK inhibitor (trametinib) caused significant downregulation of c-Myc mRNA in LS174t tumor cells. The c-Myc mRNA was measured at 72 hours following administration of the combination therapy.

Before evaluating the combination therapy the efficacy of Trametinib alone was tested in colorectal cancer. First, the LS174t tumor bearing mice were treated orally with Trametinib at 3 or 1 mg/kg dose levels for 4 days and monitored for tumor growth. FIG. 4A. Based on the efficacy data, we picked 0.3 mg/kg as the dose to use in combination with BCAT1. Based on the single agent BCAT1 efficacy studies in these tumors, we picked 3 mg/kg as the dose to be used in combination with Trametinib. With this combination, the mice bearing LS174t tumors were effectively treated (>90% growth inhibition) compared to the either of the single agent treatment. FIG. 4B. Combination therapy with BCAT1 and an MEK inhibitor also caused significant downregulation of MYC in treated tumors as compared to tumors treated with a single agent. FIG. 4C.

Figure 5A:
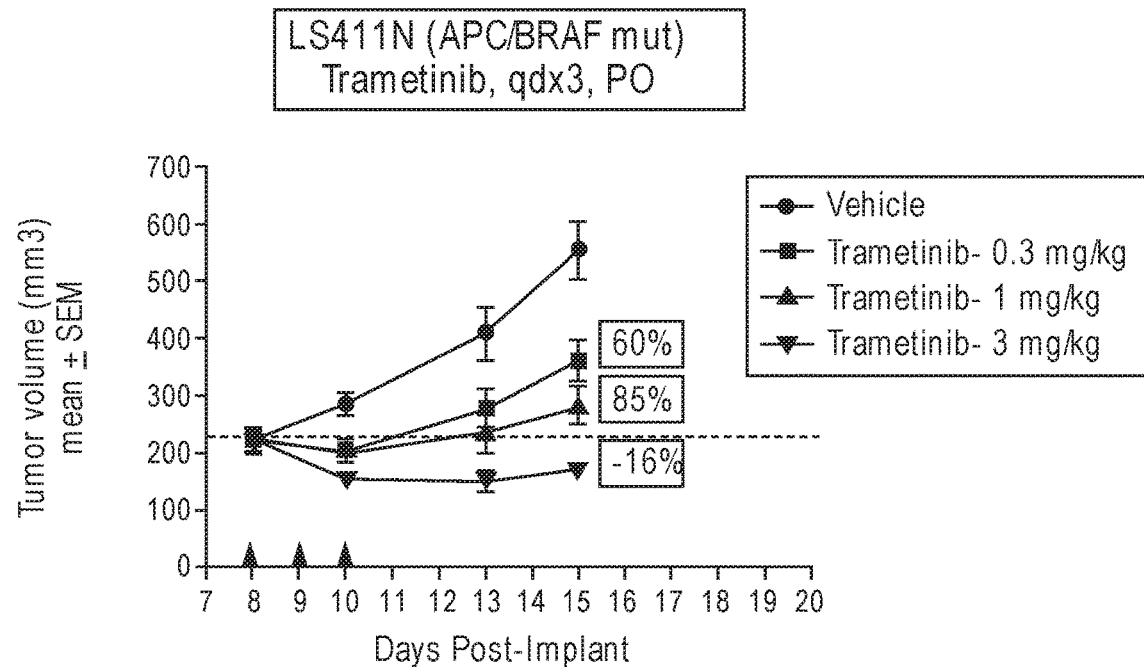
FIGS. 5A-B show that combination therapy with BCAT1 and a MEK inhibitor (trametinib) at lower dosages exhibits synergistic anti-tumor efficacy in a model of CRC using human LS411N tumor cells.
Figure 5B:
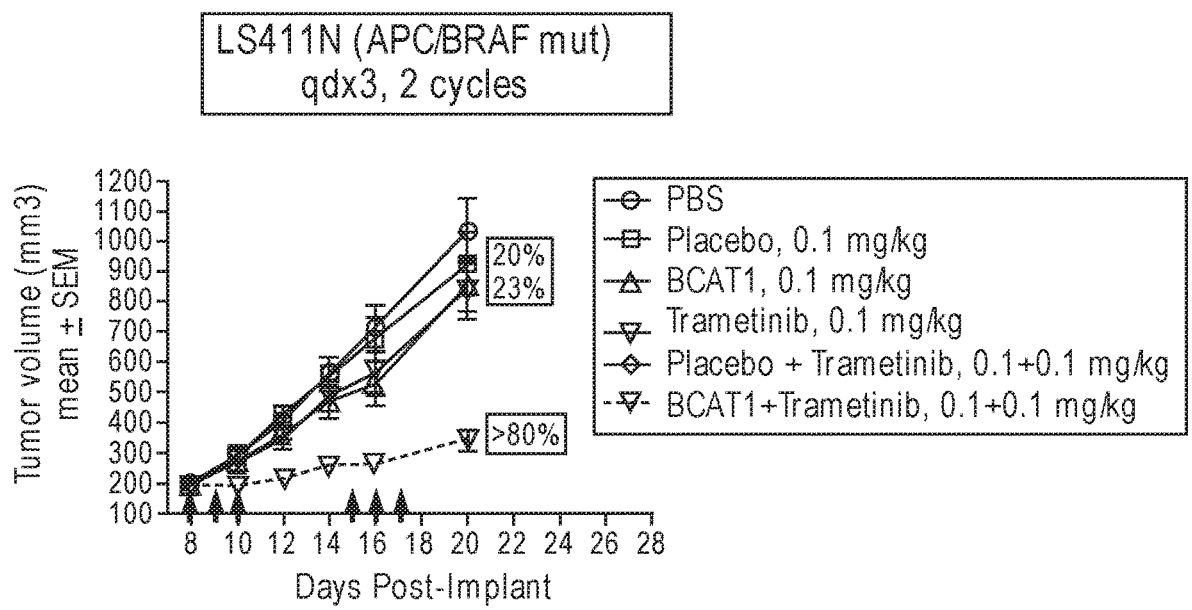

We then evaluated the single agent Trametinib in LS411N tumor bearing mice at different dose levels (3, 1 and 0.3 mg/kg) and selected 0.1 mg/kg as the dose to be used in the combination study. FIG. 5A. For BCAT1, a dose of 0.1 mg/kg was selected from the previous single agent efficacy studies to be used in combination with Trametinib to treat LS411N tumors. Surprisingly, the combination of BCAT1 and Trametinib lead to synergistic anti-tumor effects at doses as low as 0.1 mg/kg in LS411N tumors (greater than 80% growth inhibition) compared to either of the single agent treatment group (about 20% growth inhibition each). FIG. 5B.

Figure 5C:
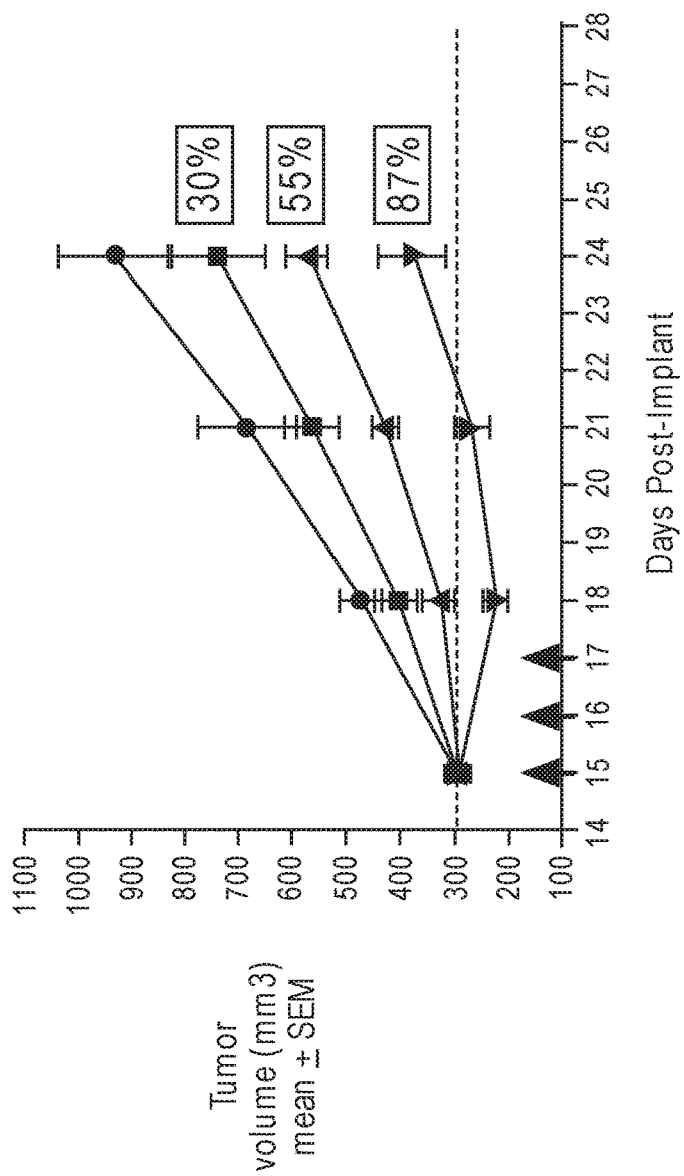
FIGS. 5C-D show that combination therapy with BCAT1 and a MEK inhibitor (trametinib) at lower dosages exhibits synergistic anti-tumor efficacy in a model of CRC using human SW403 tumor cells.
Figure 5D:
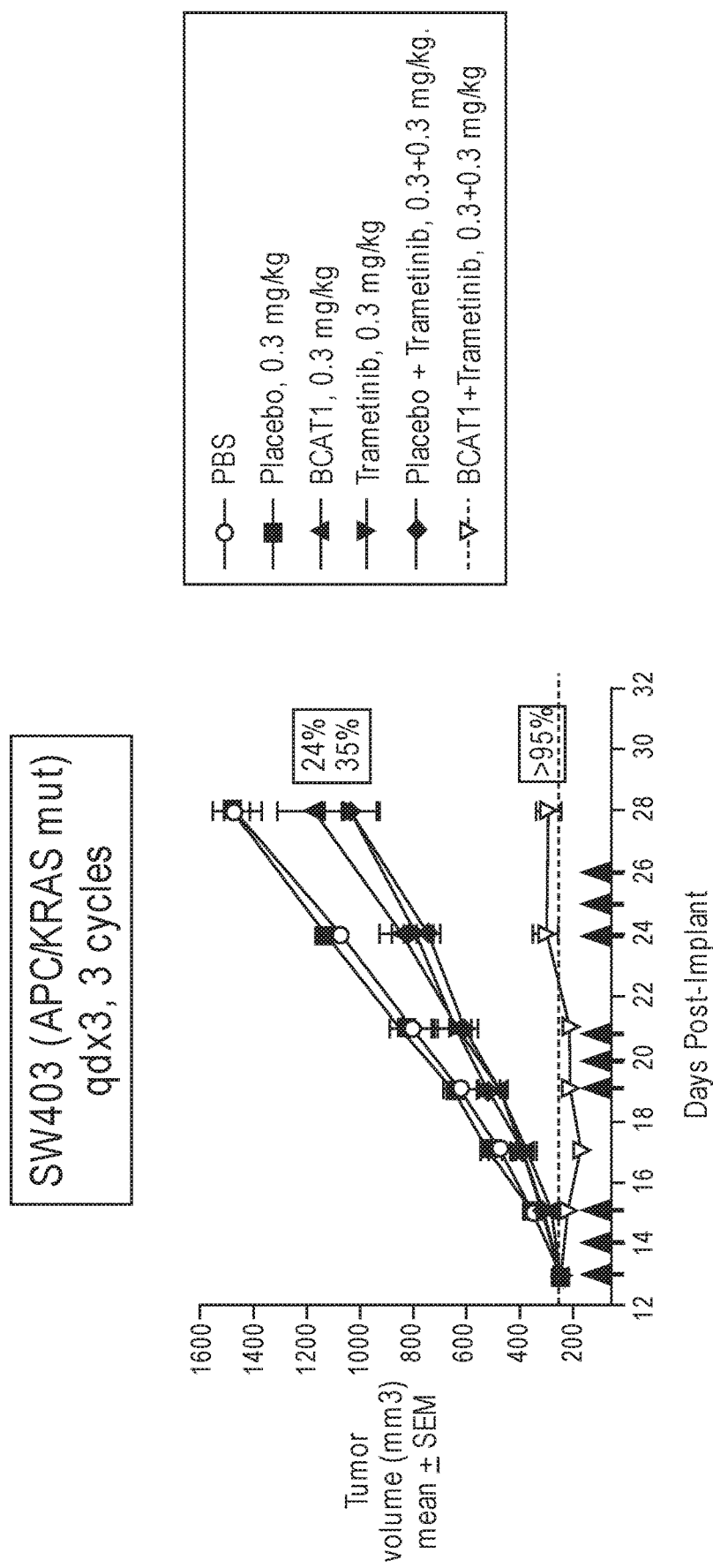

The combination treatment was also evaluated in a third CRC model (SW403) that has APC and KRAS mutations. As described for the other two models, we first checked the single agent Trametinib efficacy at different dose levels in these tumors and picked 0.3 mg/kg as the optimal dose for the combination study (FIG. 5C). BCAT1 was administered at the same dose (0.3 mg/kg) and used in combination with Trametinib. Again, the rational combination resulted in synergistic efficacy at doses as low as 0.3 mg/kg with the tumor growth inhibition over 90%, as compared to inhibition of 20% (BCAT1) and 40% (Trametinib) when each agent was administered alone (FIG. 5D).

Figure 5E:
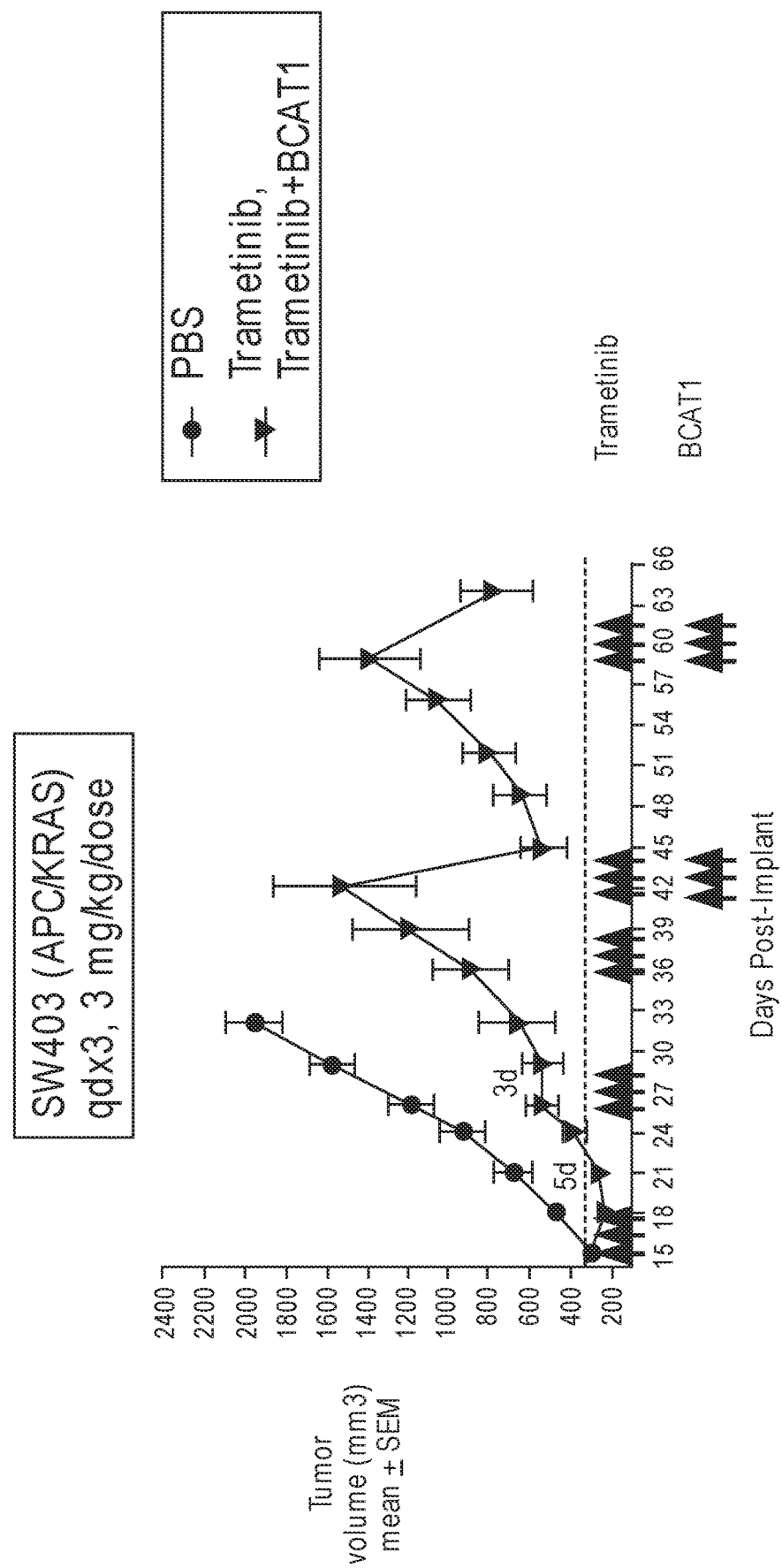
FIGS. 5E-F show that resistance to trametinib in a model of CRC using SW403 tumor cells is overcome by the administration of trametinib and BCAT1 in combination. The data represent the average tumor volume of the entire treatment groups (FIG. 5E) or each individual mouse in the treatment group (FIG. 5F).
Figure 5F:
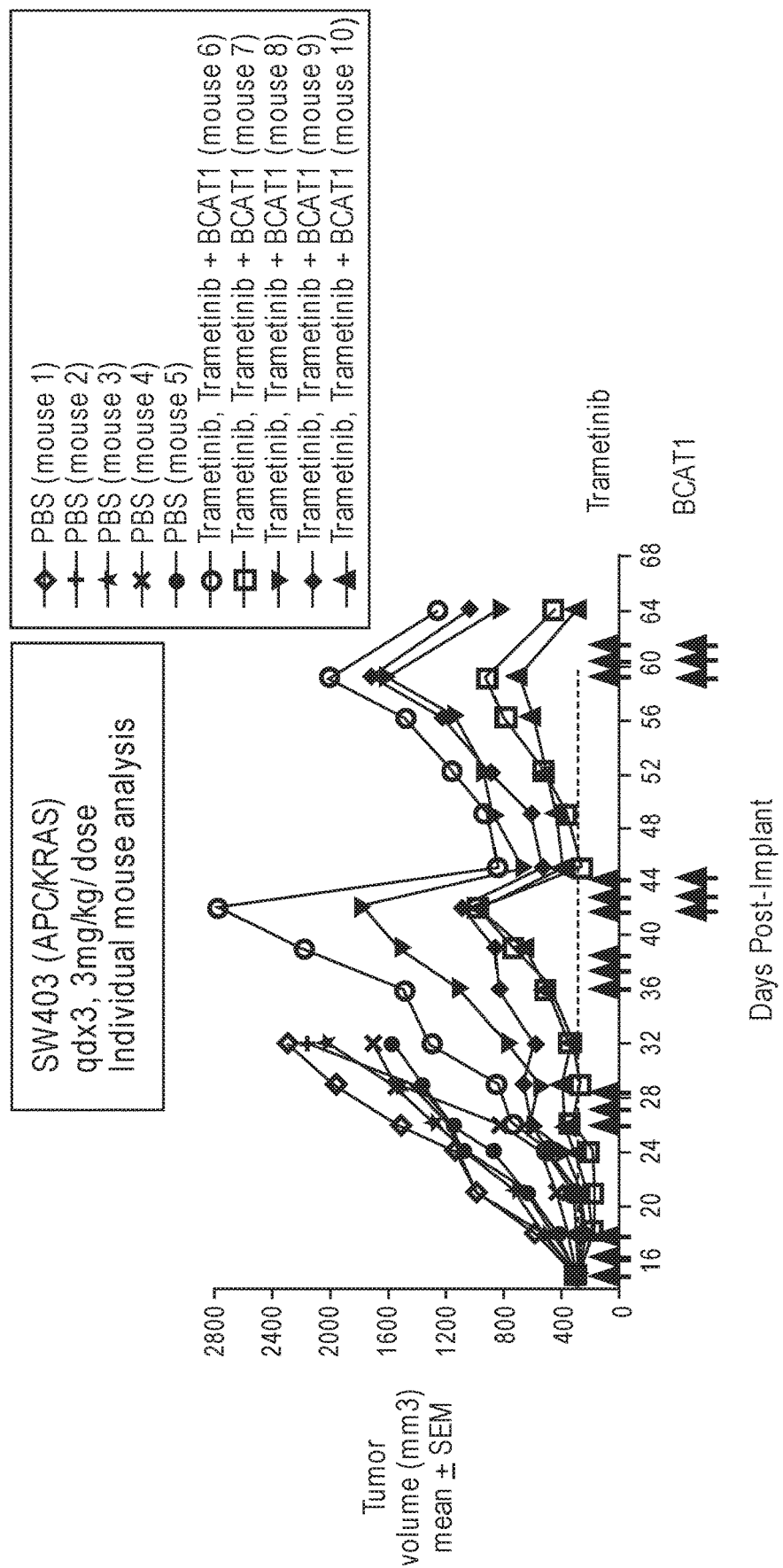

In these CRC models, tumors generally develop resistance to Trametinib over time. To investigate this resistance, SW403 tumors were continuously treated with Trametinib at 3 mg/kg doses (qdx3, 3 mg/kg×3) until the tumors stopped responding to the treatment. Once the tumors stopped responding and became resistant to Trametinib treatment, we treated the tumors with a combination of BCAT1 and Trametinib (qdx3, 3mpk+ qdx3, 3mpk) (around Day 42). Surprisingly, the tumors that failed to respond to Trametinib treatment responded nicely to the combination treatment and as a result, the average tumor volume of the treatment group was reduced by 60% within a few days after the combination treatment. It was also interesting to note that every single tumor in the treatment group responded to the combination treatment (FIGS. 5E and 5F) with a dramatic drop in tumor volume. When these tumors grew back to about the same size they were when the first round of combination treatment was administered, a second round of combination therapy was administered (around Day 60). Interestingly, these tumors responded again to the same extent that was seen after the first round of combination treatment suggesting that the BCAT1/Trametinib combination addresses the resistance developed by the tumors treated with Trametinib alone and thus provides tremendous clinical benefit in CRC patients with dual pathway activation.

Example 5: Combined Inhibition of CTNNB1 and MYC

Combination therapy with BCAT1 and a nucleic acid inhibitor molecule that targets the c-Myc gene ("MYC1") was also evaluated. MYC1 has a 25 base pair passenger strand and a 27 base pair guide strand that form a duplex region consisting of 25 base pairs, where the 3' end of the passenger strand and 5' end of the guide strand form a blunt end, and the 3' end of the guide strand consists of a single-stranded, two-base overhang. FIG. 9. The MYC1 construct was formulated in EnCore LNP.

Figure 6A:
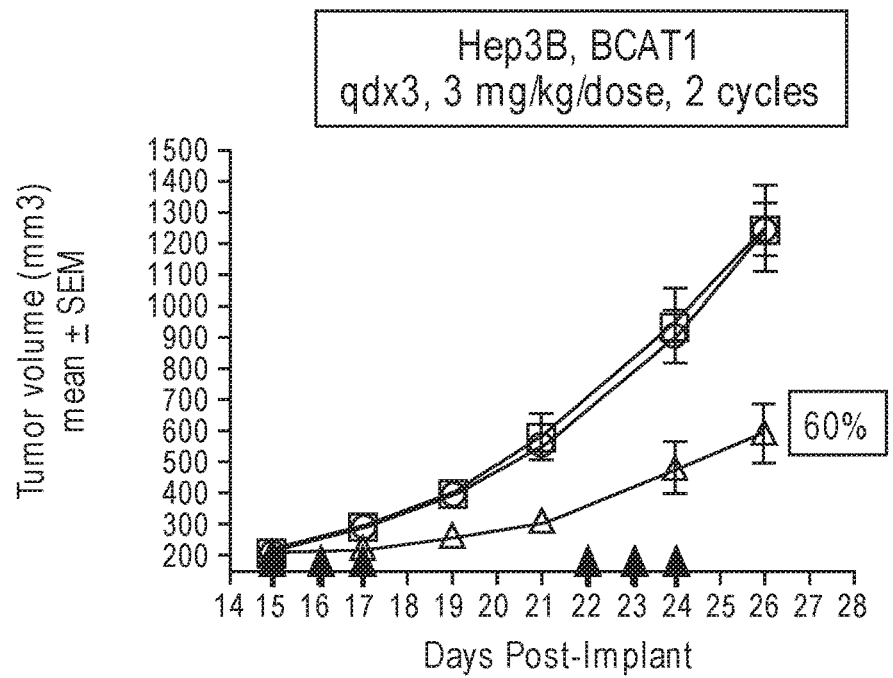
FIGS. 6A-C show that combination therapy with BCAT1 and MYC1 enhances anti-tumor efficacy as compared to treatment with either of BCAT1 or MYC1 individually. Note that when the BCAT1 and MYC1 are given in combination, the doses are one-half of the dose used when each is given individually.
Figure 6B:
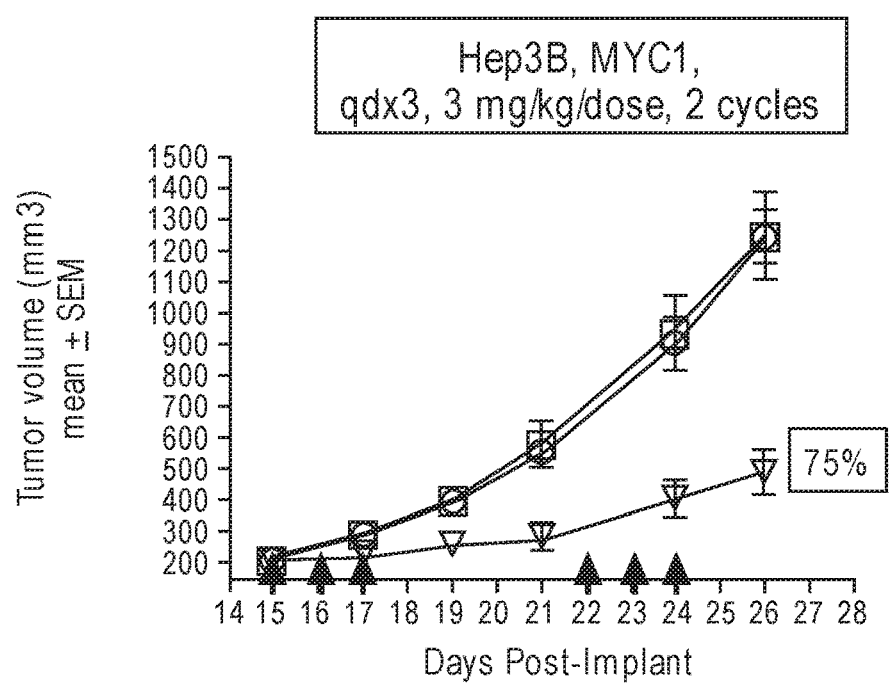
Figure 6C:
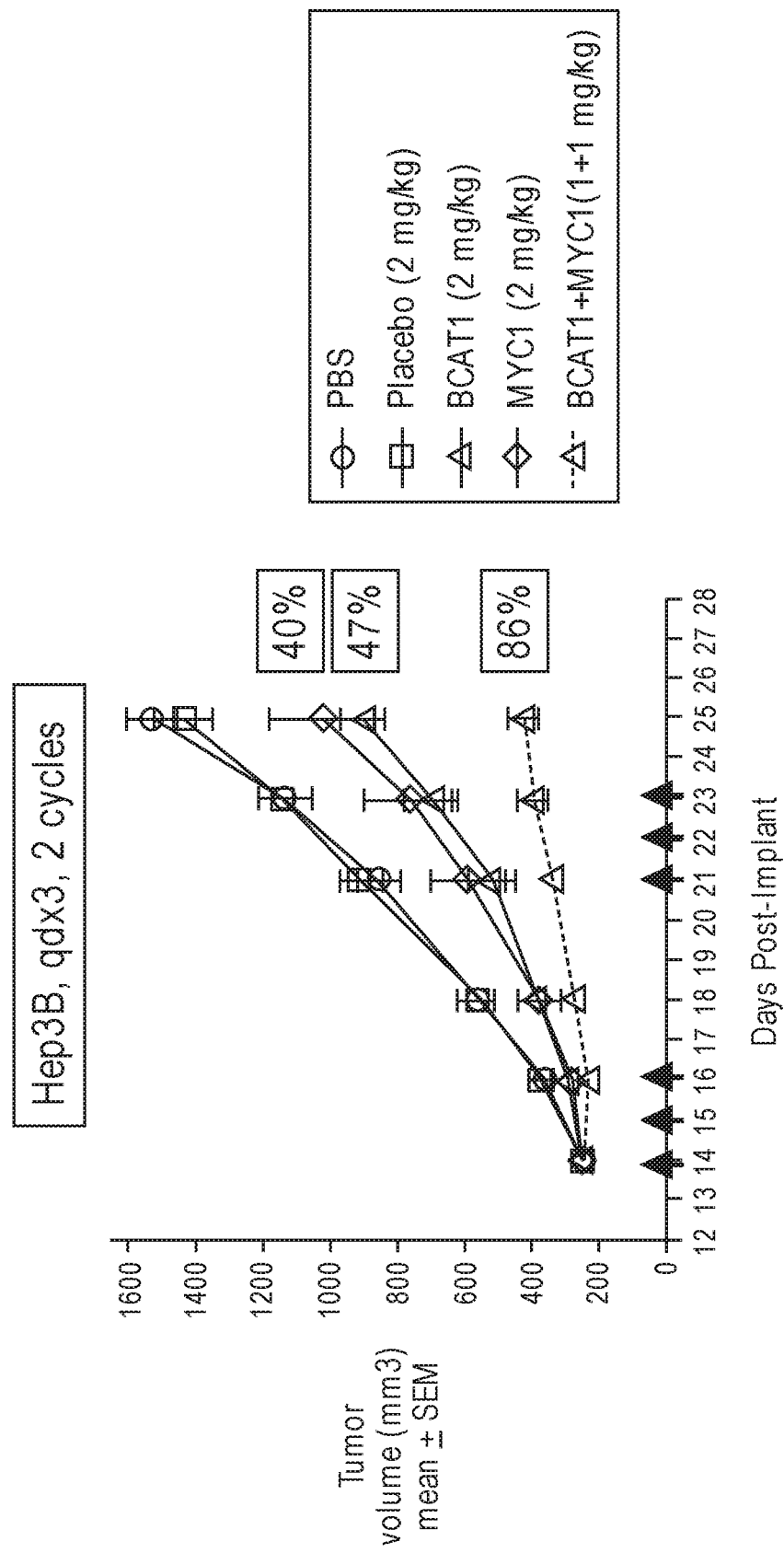
Figure 10:
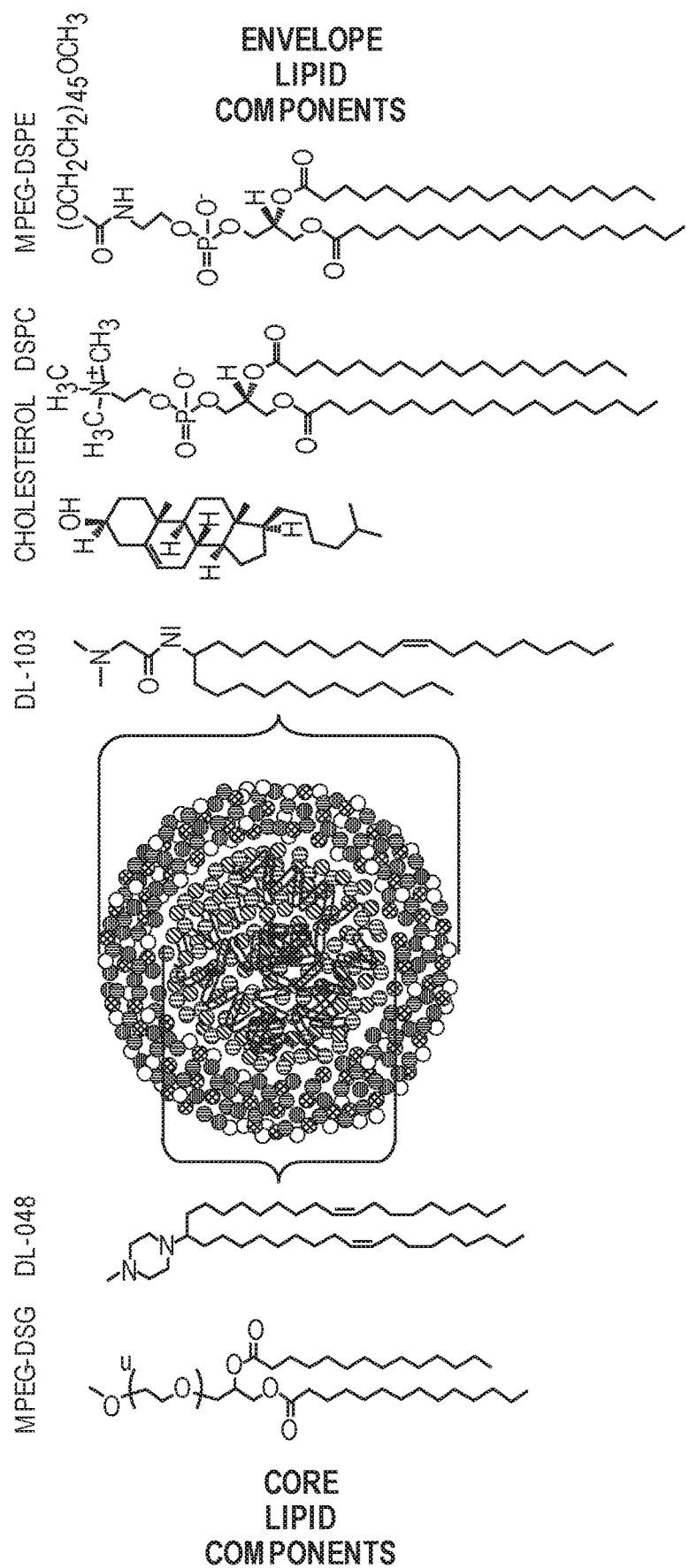
FIG. 10 shows one non-limiting embodiment of a lipid nanoparticle that can used to formulate the β-catenin or c-Myc nucleic acid inhibitor molecule. The LNP includes the following core lipids: DL-048 (cationic lipid) and DSG-MPEG (pegylated lipid), and the following envelope lipids: DL-103 (cationic lipid), DSPC, cholesterol, and DSPE-MPEG (pegylated lipid).

The single agent efficacy of BCAT1 and MYC1 at a dosage of 3 mg/kg was evaluated in a PDX mouse model bearing Hep3B tumors. FIGS. 6A and 6B. When combined at a dosage of 1 mg/kg each, BCAT1 and MYC1 demonstrated a robust anti-tumor efficacy (86%), as compared to MYC1 and BCAT1 administered individually at 2 mg/kg (40% and 47% growth inhibition, respectively). FIG. 6C.

Example 6: Treatment of Liver Metastases with Combination of BCAT1 and Trametinib In addition to evaluating the combination BCAT1 and trametinib in subcutaneous tumors with dual pathway activation, we also evaluated this combination in mice bearing CRC liver metastases. The primary metastatic site of CRC is liver, and most of the CRC patients are reported to die mainly of CRC liver metastases.

Figure 11A:
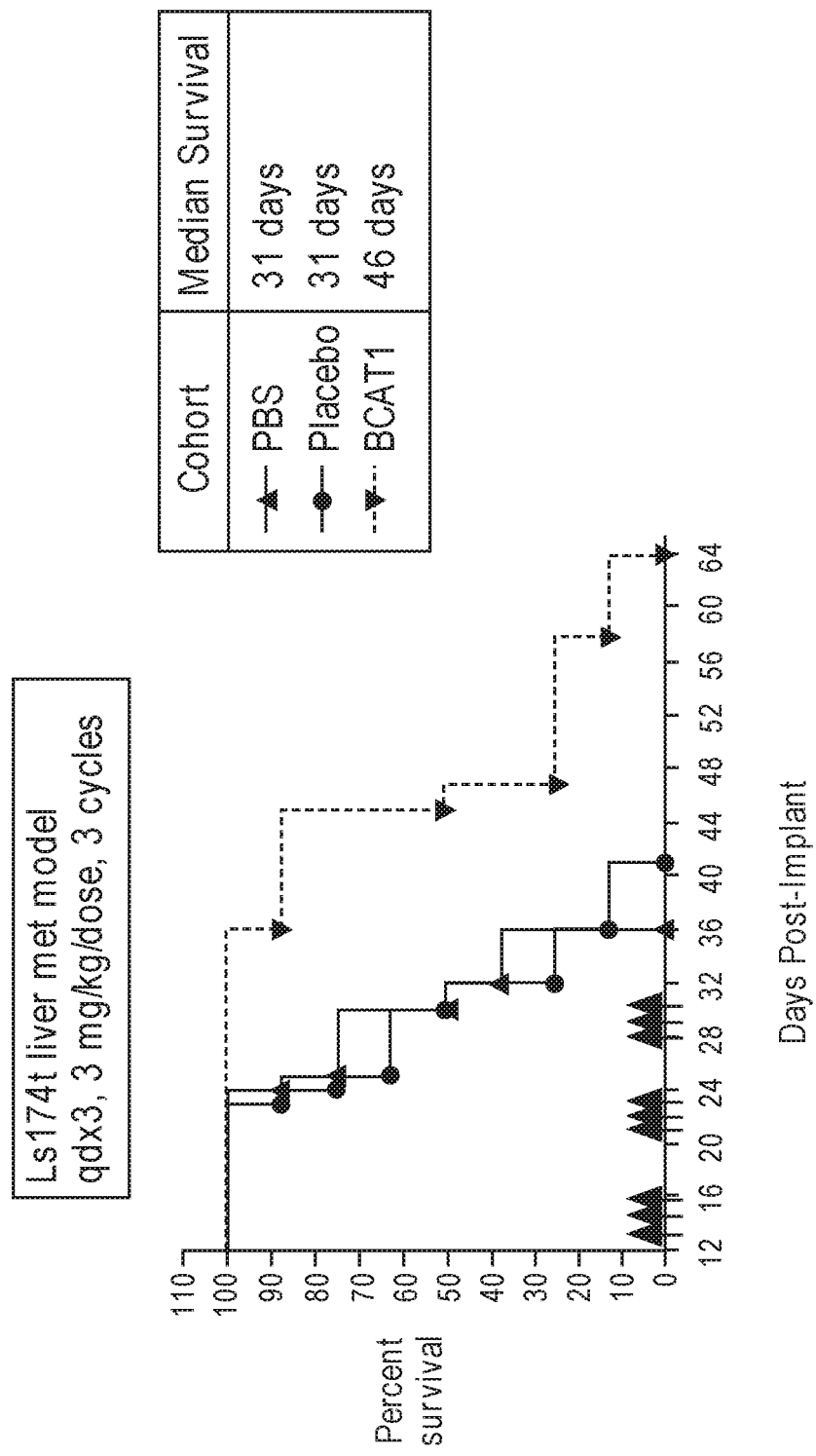
FIG. 11A-B show that administration of BCAT1 (qdx3, 3 mg/kg/dose, 3 cycles) improves survival as compared to PBS or placebo in a Ls174t CRC liver metastases model (FIG. 11A) or a LS411N CRC liver metastases model (FIG. 11B).

We developed multiple CRC liver metastatic models by surgically implanting Ls174t and LS411N cells in spleen. 2-5 weeks after implanting $2 \times 10^6$ cells, the primary Ls174t tumors grown in the spleen spontaneously metastasized to the liver. To see if BCAT1 monotherapy will treat both primary and metastatic tumors and improve survival, 2 weeks after the tumor implantation, mice bearing Ls174t tumors were treated with BCAT1 or placebo at 3 mg/kg doses (qdx3, 3 mg/kg, 3 cycles). As shown in FIG. 11A, all the mice that received PBS or placebo treatment died in 42 days, whereas the mice that received BCAT1 treatment survived for a longer period of time. The mean survival time ("MST") of the control-treated group is 31 days, whereas the MST of the BCAT1-treated group is 46 days).

Figure 11B:
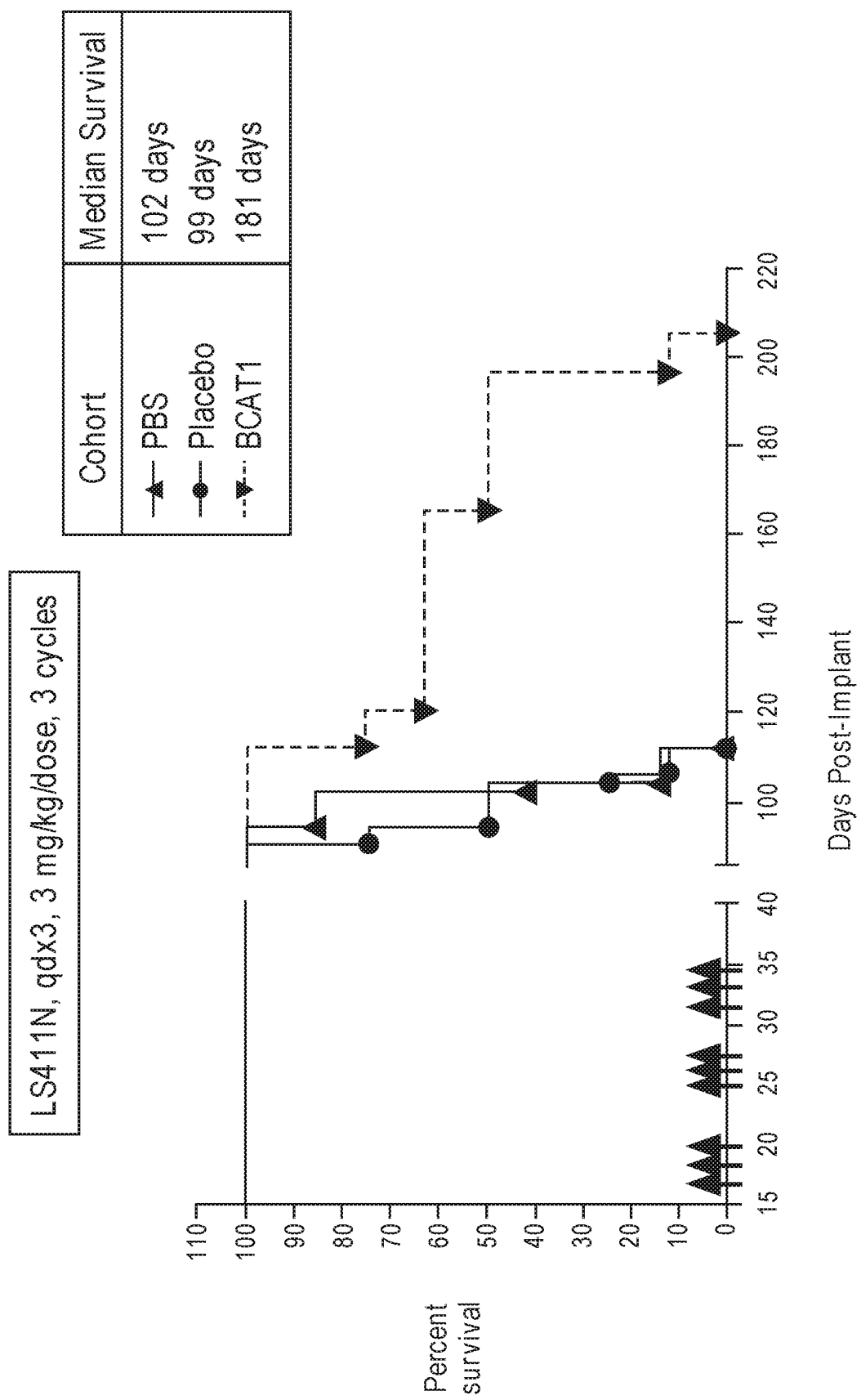

Similarly, the mice with LS411N liver metastases were also treated with BCAT1 or controls (placebo or PBS) at the same dose levels for 3 weeks. Unlike the Ls174t tumors, LS411N tumors took a much longer time to metastasize to the liver after implanting $2 \times 10^6$ cells in the spleen. The treatment was initiated 18 days after the implantation of LS411N cells in the spleen. It took 112 days for all the control treated mice to die. BCAT1 monotherapy however improved the survival of the mice bearing LS411N liver metastases significantly compared to control treated groups, with 75% of BCAT1-treated mice surviving at 112 days post-implant (FIG. 11B). It took about 6 months for all of the BCAT1-treated mice to die. In summary, BCAT treatment extended the survival of mice bearing LS411N liver metastasis by up to two-fold compared to the control treatment groups (MST of PBS/Placebo treatment groups is 99-102 days, whereas the MST of the BCAT1-treated group is 181 days).

Figure 11C:
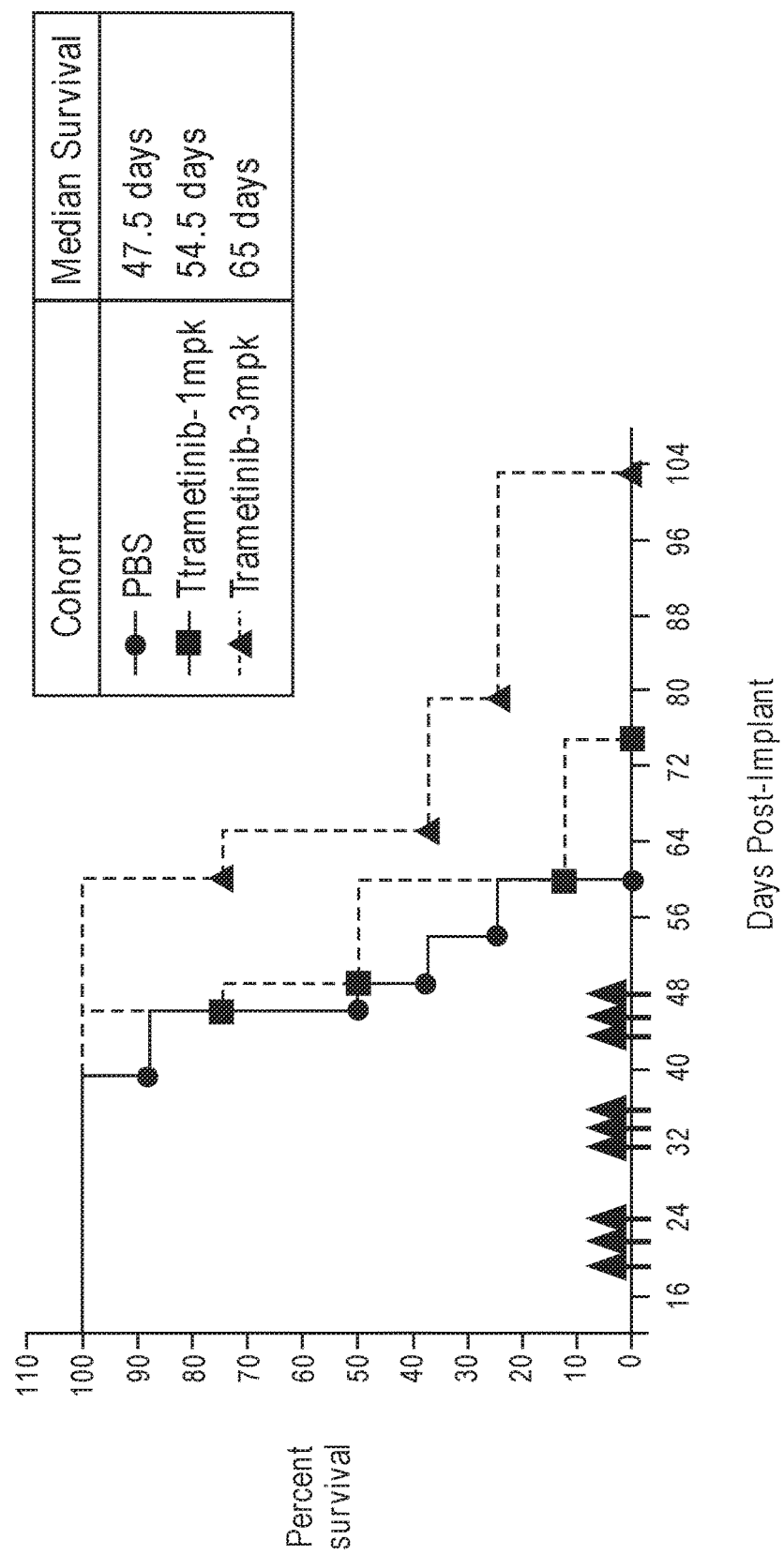
FIG. 11C shows that administration of trametinib (qdx3, 1 or 3 mg/kg/dose, 3 cycles) improves survival in a Ls174t CRC liver metastases model as compared to PBS.
Figure 11D:
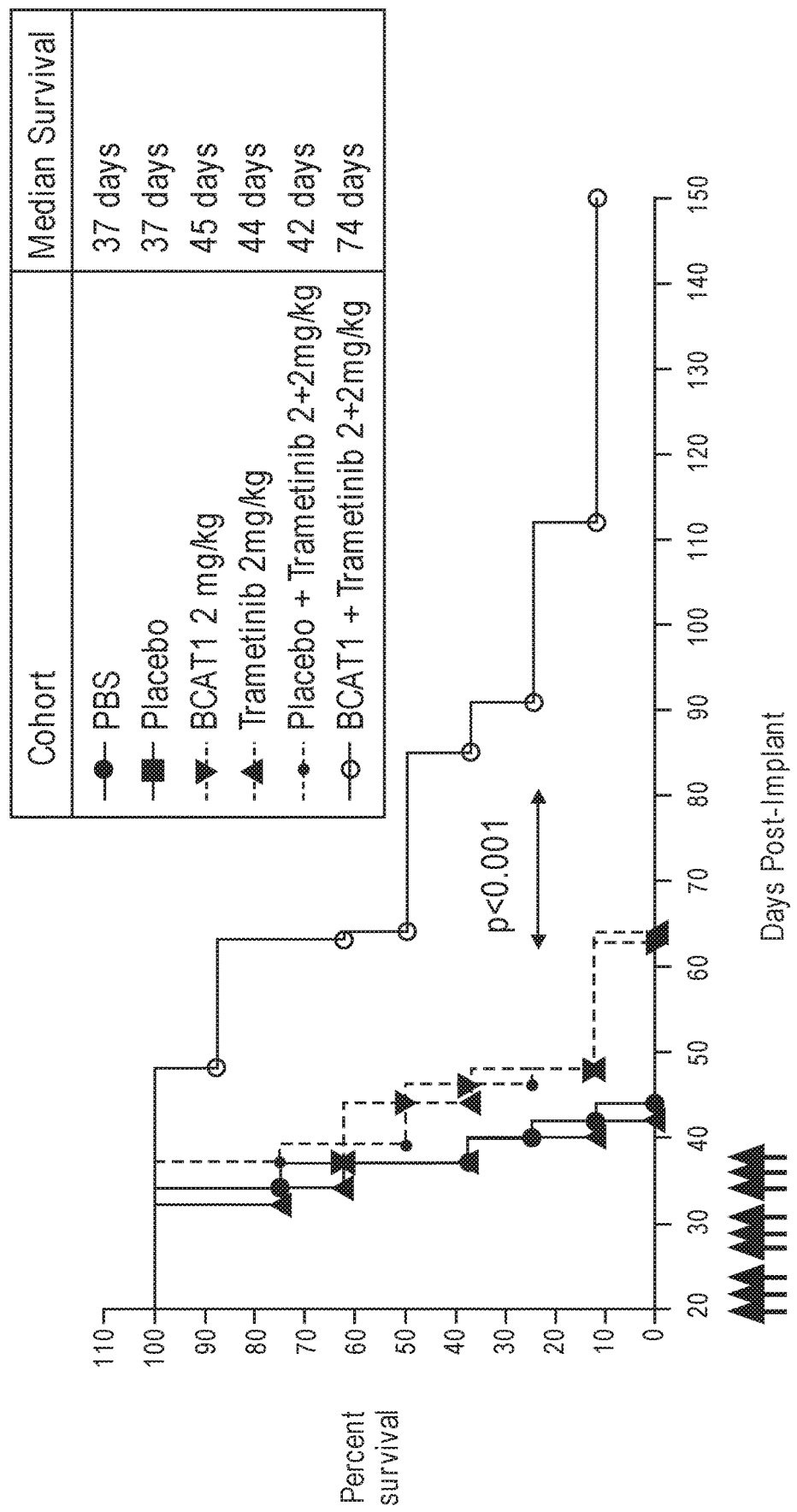
FIG. 11D compares combination therapy with BCAT1 and trametinib (qdx3, 2 mg/kg/dose, 3 cycles) to individual treatment with BCAT1 or trametinib in a Ls174t CRC liver metastases model and suggests a synergistic response for the combination therapy.

Before we evaluated the combination strategies in these CRC metastatic models, we ran a single agent Trametinib efficacy in the Ls174t liver metastatic model. Fewer number of Ls174t cells ($1 \times 10^6$ cells) were implanted in the spleen this model to reduce the aggressiveness of the tumor progression. 18 days after the implantation, mice were randomly distributed into 3 groups and treated with PBS, Trametinib at 1 mg/kg or Trametinib at 3 mg/kg dose levels (qdx3, 3 cycles). As shown in FIG. 11C, the lower dose of Trametinib (1 mg/kg) did not show much benefit in survival as compared to the PBS treated group (MST of 47 days vs. 54 days), whereas the higher dose Trametinib (3 mg/kg) significantly extended the survival compared to PBS treated group (MST of 65 days).

Next we ran a combination efficacy study in mice bearing Ls714t liver metastasis based on the doses used in the single agent efficacy studies. This time, the treatment was initiated 3 weeks after tumor implantation of $2 \times 10^6$ Ls174t cells. BCAT1, Placebo, and Trametinib were dosed at 2 mg/kg and the combination groups (Placebo+Trametinib or BCAT1+Trametinib) were dosed at 2+2 mg/kg. In this instance, because the treatment was initiated well after the metastasis process started, and the dose levels were slightly reduced, each of the single agent treatments demonstrated only minor improvement in the survival. All the mice in both control groups (placebo and PBS) died in 44 days (median survival of 37 days). 90% of the mice that had either BCAT1, Trametinib, or Placebo and Trametinib treatment died around day 48 (median survival of 45, 44 or 42 days). One mouse in each of these groups survived a little longer and died on day 64. Strikingly, the BCAT1 and Trametinib combination provided a dramatic survival benefit (median survival of 74 days) with 2 mice surviving over 100 days and one mouse surviving over 200 days. As such, mice with advanced liver metastases were treated effectively with the rational combination of BCAT1 and Trametinib. The combination of BCAT1 and Trametinib, thus, provides tremendous clinical benefit for metastatic CRC patients with dual pathway activation.

Unless otherwise indicated, all numbers used in the specification and claims are to be understood as being modified in all instances by the term "about," whether or not so stated. It should also be understood that the precise numerical values used in the specification and claims form additional embodiments of the disclosure, as do all ranges and subranges within any specified endpoints. In addition, it will be noted that where steps are disclosed, the steps need not be performed in that order unless explicitly stated.

Other embodiments will be apparent to those skilled in the art from consideration of the specification and practice of the disclosure.

What is claimed is:

1. A method of treating a β-catenin-associated cancer in a subject, comprising administering to the subject:
   a therapeutically effective amount of a β-catenin nucleic acid inhibitor molecule; and
   a therapeutically effective amount of a MEK inhibitor, wherein the β-catenin-associated cancer is a colorectal cancer that has metastasized to the liver, and
   wherein the β-catenin nucleic acid inhibitor molecule is a dsRNAi inhibitor molecule.

2. The method of claim 1, wherein the MEK inhibitor is trametinib.

3. The method of claim 1, wherein the subject is a human.

4. The method of claim 1, wherein the β-catenin nucleic acid inhibitor molecule is a dsRNAi inhibitor molecule, and wherein the double-stranded region of the molecule is between 15 and 40 nucleotides in length.

5. The method of claim 1, wherein the β-catenin nucleic acid inhibitor molecule is a dsRNAi inhibitor molecule comprising a sense and an antisense strand and a duplex region of between 18 and 40 nucleotides, wherein the sense strand is 25-34 nucleotides in length and the antisense strand is 26-38 nucleotides in length and comprises 1-5 single-stranded nucleotides at its 3'-terminus.

6. The method of claim 5, wherein the sense strand comprises the sequence of SEQ ID NO: 1 and the antisense strand comprises the sequence of SEQ ID NO: 2.

7. The method of claim 1, wherein the β-catenin nucleic acid inhibitor molecule is formulated with a lipid nanoparticle.

8. The method of claim 7, wherein the lipid nanoparticle comprises a cationic lipid and a pegylated lipid.

9. The method of claim 1, wherein prior to administering the β-catenin nucleic acid inhibitor molecule, the subject has undergone prior treatment for the β-catenin-associated cancer and developed resistance to that treatment.

10. The method of claim 9, wherein the prior treatment is administration of a MEK inhibitor.

11. The method of claim 10, wherein the MEK inhibitor of the prior treatment is trametinib.

12. The method of claim 10, wherein the MEK inhibitor administered to the subject is trametinib.

13. The method of claim 11, wherein the MEK inhibitor administered to the subject is trametinib.

14. The method of claim 1, wherein prior to administering the β-catenin nucleic acid inhibitor molecule, the subject has undergone at least two administrations of a prior treatment for the β-catenin-associated cancer.

15. The method of claim 14, wherein the prior treatment is administration of a MEK inhibitor.

16. The method of claim 15, wherein the MEK inhibitor of the prior treatment is trametinib.

17. The method of claim 15, wherein the MEK inhibitor administered to the subject is trametinib.

18. The method of claim 16, wherein the MEK inhibitor administered to the subject is trametinib.

19. The method of claim 1, wherein the treatment reduces metastases in the subject.

* * * * *

SEQUENCE LISTING

```
<160> NUMBER OF SEQ ID NOS: 6

<210> SEQ ID NO 1
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
agaauacaaa ugauguagaa acagcc                                              26

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
uagcuaucgt ggcuguuucu acaucauuug uauucugc                                 38

<210> SEQ ID NO 3
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
agcuuuuuug cccugcguga ccagac                                              26

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
uagcuaucgt gucuggucac gcagggcaaa aaagcucc                                 38

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
agcuuuuuug cccugcguga ccaga                                          25

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucuggucacg cagggcaaaa aagcucc                                        27
```